United States Patent
Tung et al.

(10) Patent No.: US 9,952,151 B2
(45) Date of Patent: Apr. 24, 2018

(54) SURFACE FEATURES BY AZIMUTHAL ANGLE

(71) Applicant: Seagate Technology LLC, Cupertino, CA (US)

(72) Inventors: David M. Tung, Livermore, CA (US); Joachim W. Ahner, Livermore, CA (US)

(73) Assignee: Seagate Technology LLC, Cupertino, CA (US)

(*) Notice: Subject to any disclaimer, the term of this patent is extended or adjusted under 35 U.S.C. 154(b) by 0 days.

(21) Appl. No.: 15/293,000

(22) Filed: Oct. 13, 2016

(65) Prior Publication Data

US 2017/0030831 A1    Feb. 2, 2017

Related U.S. Application Data

(63) Continuation of application No. 14/096,001, filed on Dec. 3, 2013, now Pat. No. 9,513,215.

(60) Provisional application No. 61/829,157, filed on May 30, 2013.

(51) Int. Cl.
G01N 21/88 (2006.01)
G01N 21/47 (2006.01)
G01N 21/95 (2006.01)

(52) U.S. Cl.
CPC ..... *G01N 21/4738* (2013.01); *G01N 21/8806* (2013.01); *G01N 21/95* (2013.01); *G01N 2021/8809* (2013.01); *G01N 2201/062* (2013.01); *G01N 2201/12* (2013.01)

(58) Field of Classification Search
CPC .... G01N 21/95; G01N 21/9506; G01N 21/94; G01N 21/47; G01N 21/4738; G01N 21/9501
USPC .... 356/237.1–237.5; 382/100, 103, 307–308
See application file for complete search history.

(56) References Cited

U.S. PATENT DOCUMENTS

| | | | | |
|---|---|---|---|---|
| 9,201,019 | B2* | 12/2015 | Tung | G01N 21/88 |
| 9,217,714 | B2* | 12/2015 | Ahner | G01N 21/95 |
| 9,217,715 | B2* | 12/2015 | Ahner | G01N 21/4738 |
| 9,274,064 | B2* | 3/2016 | Ahner | G01N 23/20 |
| 9,297,751 | B2* | 3/2016 | Ahner | G01N 21/95 |
| 9,297,759 | B2* | 3/2016 | Ahner | G01N 21/63 |
| 9,377,394 | B2* | 6/2016 | Ahner | G01N 21/95 |
| 9,488,594 | B2* | 11/2016 | Ahner | G01N 23/20 |

(Continued)

FOREIGN PATENT DOCUMENTS

| | | |
|---|---|---|
| CN | 101563589 A | 10/2009 |
| CN | 102141526 A | 8/2011 |
| WO | 2006-041944 A2 | 4/2006 |

OTHER PUBLICATIONS

CN First Office Action dated Mar. 28, 2017 in CN Application No. 201480030129.5, Includes English Translation. 22 pages.

(Continued)

*Primary Examiner* — Hoa Pham

(57) ABSTRACT

Provided herein is an apparatus, including a photon emitter configured to emit photons onto a surface of an article at a number of azimuthal angles; and a processing element configured to process photon-detector-array signals corresponding to photons scattered from surface features of the article and generate one or more surface features maps for the article from the photon-detector-array signals corresponding to the photons scattered from the surface features of the article.

20 Claims, 12 Drawing Sheets

(56) References Cited

U.S. PATENT DOCUMENTS

| | | | | |
|---|---|---|---|---|
| 9,513,215 B2* | 12/2016 | Tung | ............... | G01N 21/4738 |
| 2004/0207836 A1* | 10/2004 | Chhibber | ........... | G01N 21/4738 |
| | | | | 356/237.4 |
| 2016/0069799 A1* | 3/2016 | Ahner | ................... | G01N 21/95 |
| | | | | 356/446 |
| 2016/0069814 A1* | 3/2016 | Tung | ..................... | G01N 21/88 |
| | | | | 356/237.3 |
| 2016/0069815 A1* | 3/2016 | Ahner | ............... | G01N 21/4738 |
| | | | | 356/237.3 |
| 2016/0169802 A1* | 6/2016 | Ahner | .................. | G01N 21/63 |
| | | | | 356/237.2 |
| 2016/0274037 A1* | 9/2016 | Ahner | .................. | G01N 21/95 |

OTHER PUBLICATIONS

SG Invitation to Respond to Written Opinion dated Feb. 20, 2017 in SG Application No. 11201509699T. 6 pages.
CN Second Office Action dated Sep. 22, 2017 in CN Application No. 201480030129.5, Includes English Translation. 20 pages.

* cited by examiner

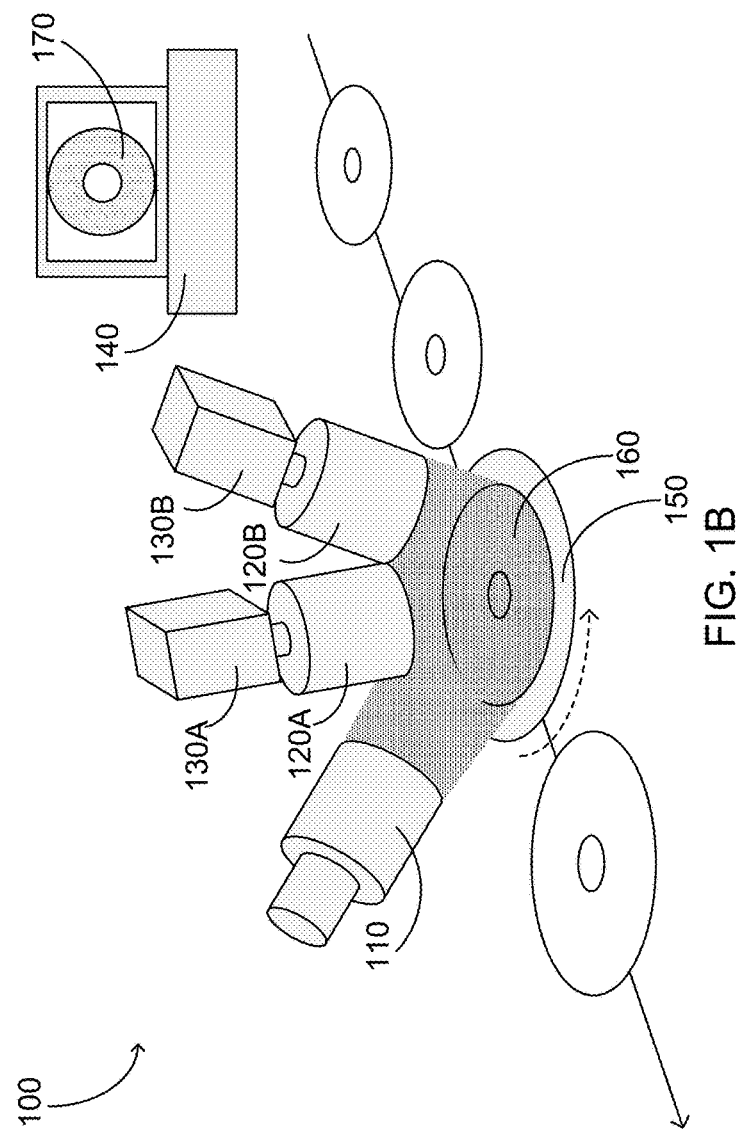

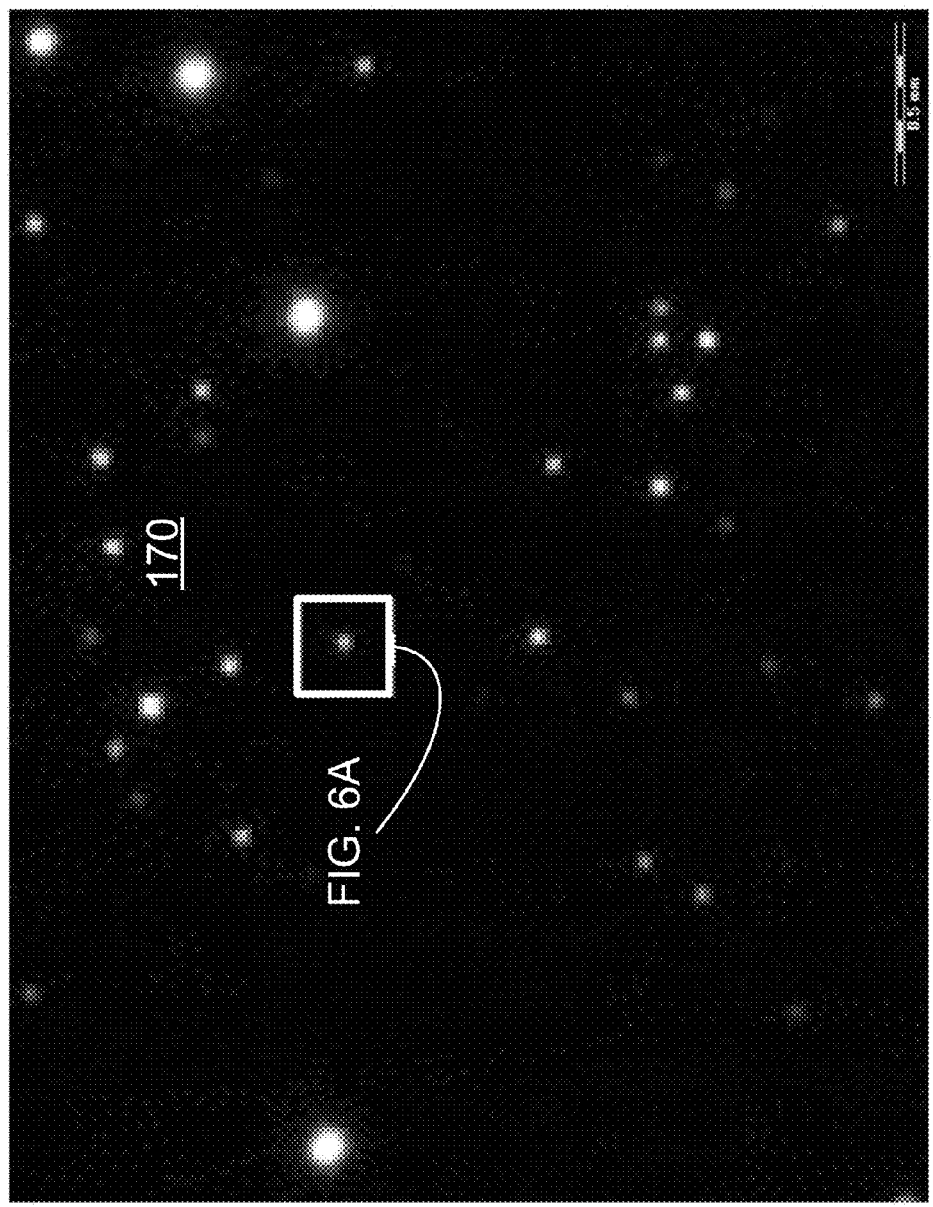

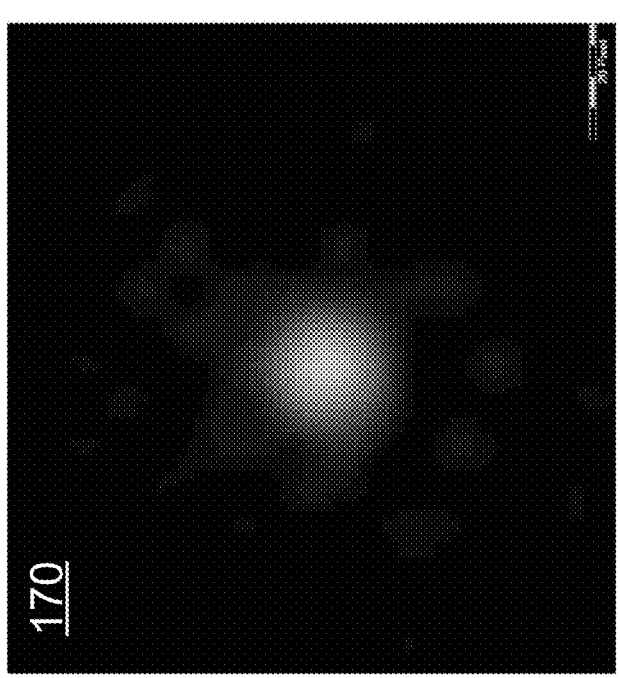
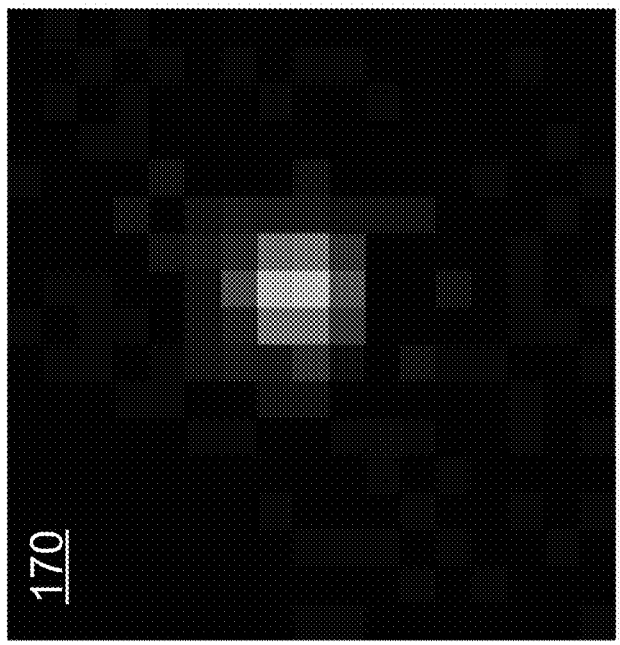
FIG. 6A
FIG. 6B

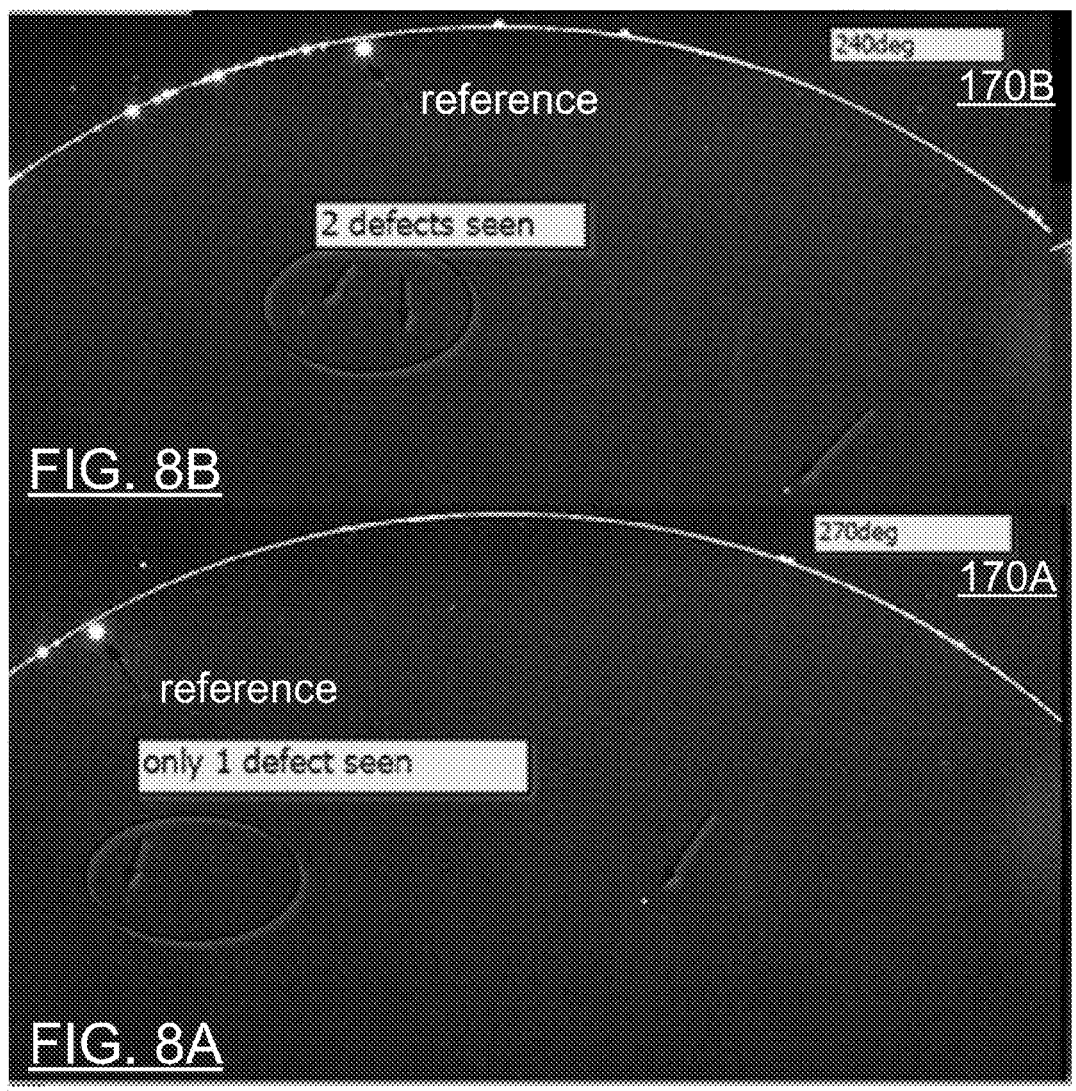

SURFACE FEATURES BY AZIMUTHAL ANGLE

CROSS REFERENCE

This application is a continuation application and claims the benefit and priority to the U.S. patent application Ser. No. 14/096,001, filed on Dec. 3, 2013 which claims the benefit and priority to the U.S. Provisional Patent Application No. 61/829,157, filed May 30, 2013, all of which are incorporated herein by reference.

BACKGROUND

An article fabricated on a production line may be inspected for certain features, including defects that might degrade the performance of the article or a system including the article. For example, a hard disk for a hard disk drive may be fabricated on a production line and inspected for certain surface features, including surface and subsurface defects that might degrade the performance of the disk or the hard disk drive. Accordingly, apparatuses and methods may be used to inspect articles for features such as defects.

SUMMARY

Provided herein is an apparatus, including a photon emitting means configured to emit photons onto a surface of an article at a number of azimuthal angles; and a processing means configured to process photon-detector-array signals corresponding to photons scattered from surface features of the article and generate one or more surface features maps for the article from the photon-detector-array signals corresponding to the photons scattered from the surface features of the article.

These and other features and aspects of the concepts provided herein may be better understood with reference to the following drawings, description, and appended claims.

DRAWINGS

Figure 1A:
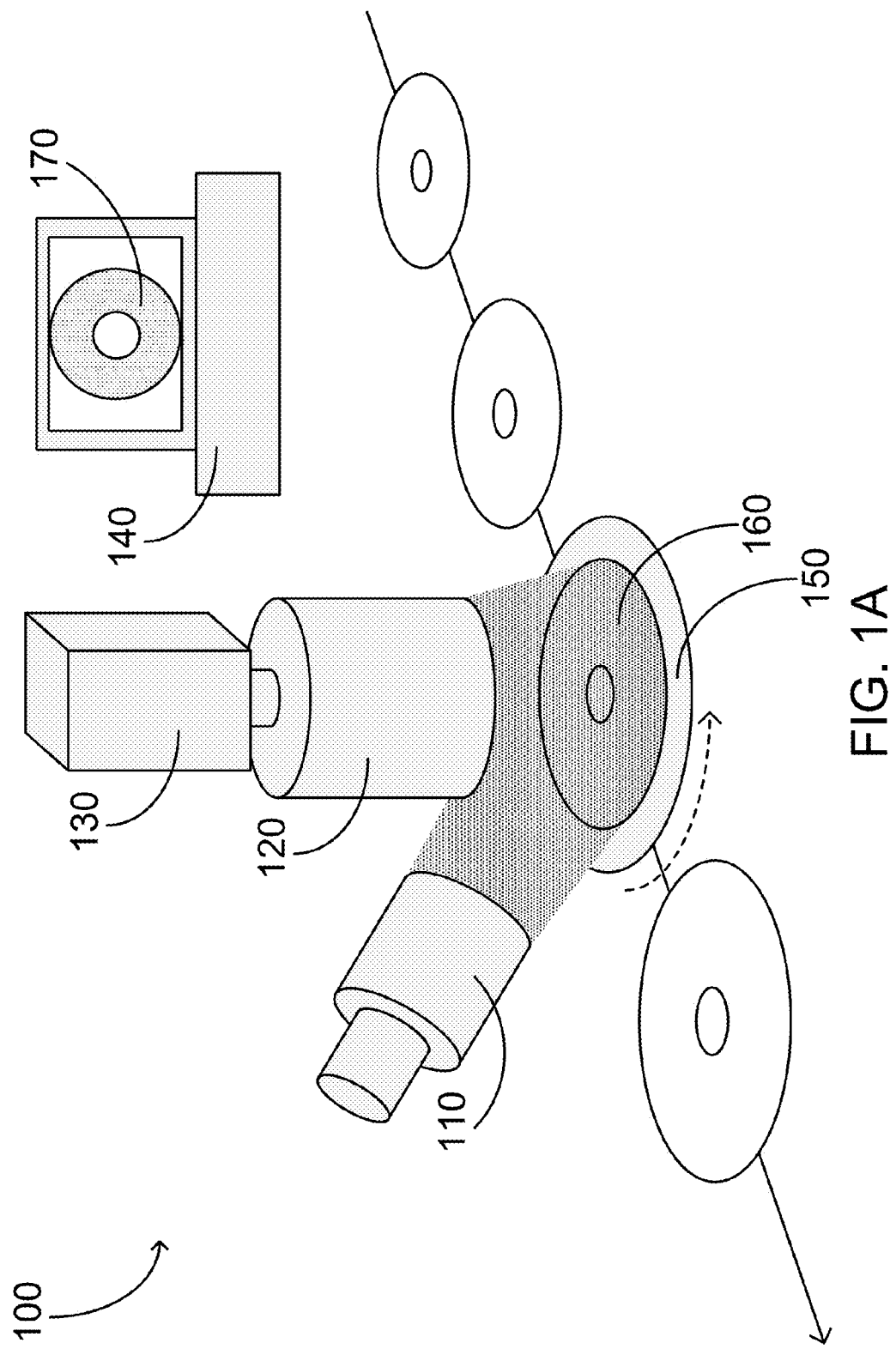

FIG. 1A-1B provide a schematic illustrating detection of surface features of articles according to one aspect of the present embodiments.

Figure 2:
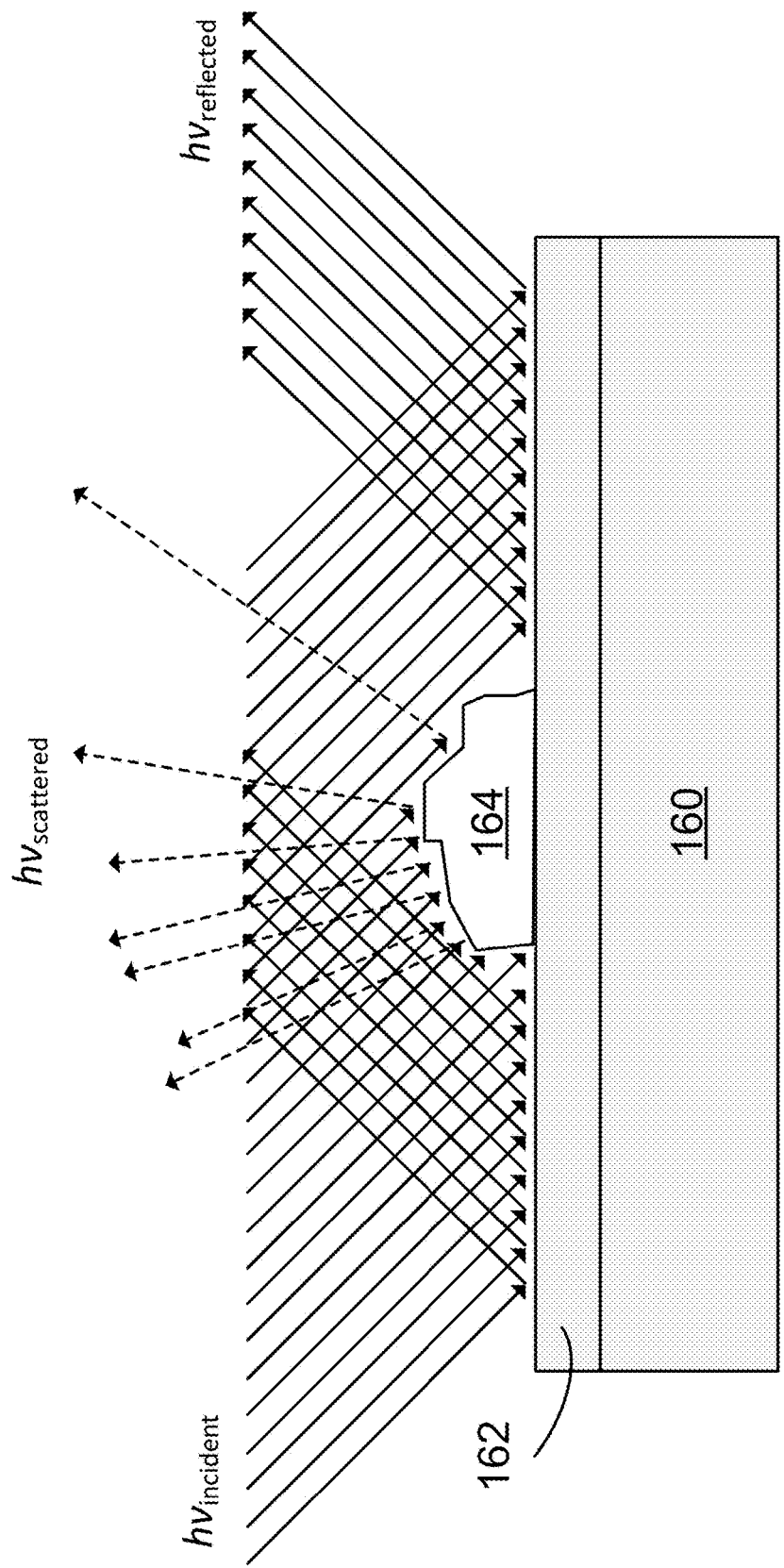

FIG. 2 provides a schematic illustrating photon scattering from a surface feature of an article according to one aspect of the present embodiments.

Figure 3:
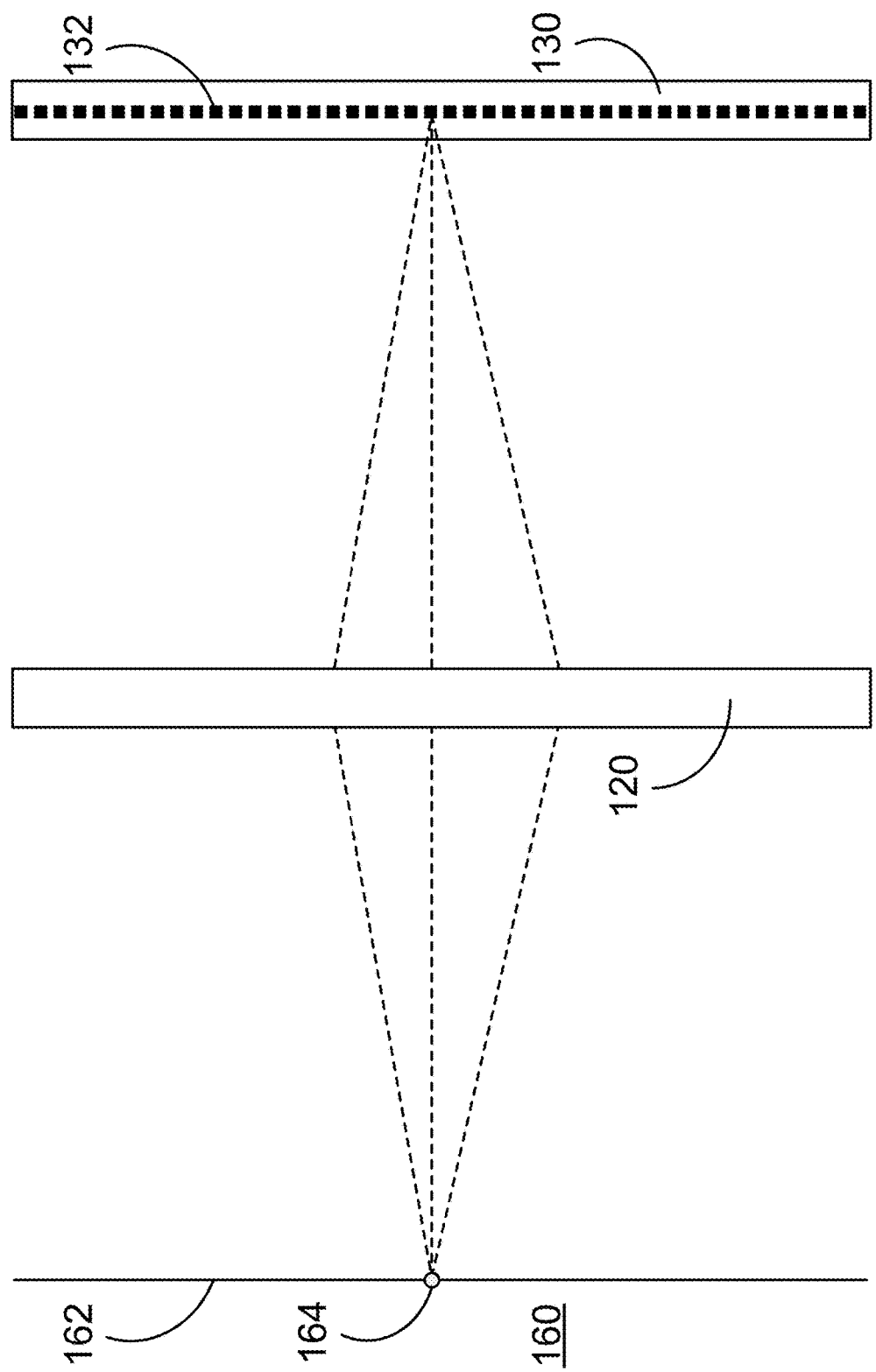

FIG. 3 provides a schematic illustrating photons scattering from a surface feature of an article, through an optical component, and onto a photon detector array according to one aspect of the present embodiments.

Figure 4:
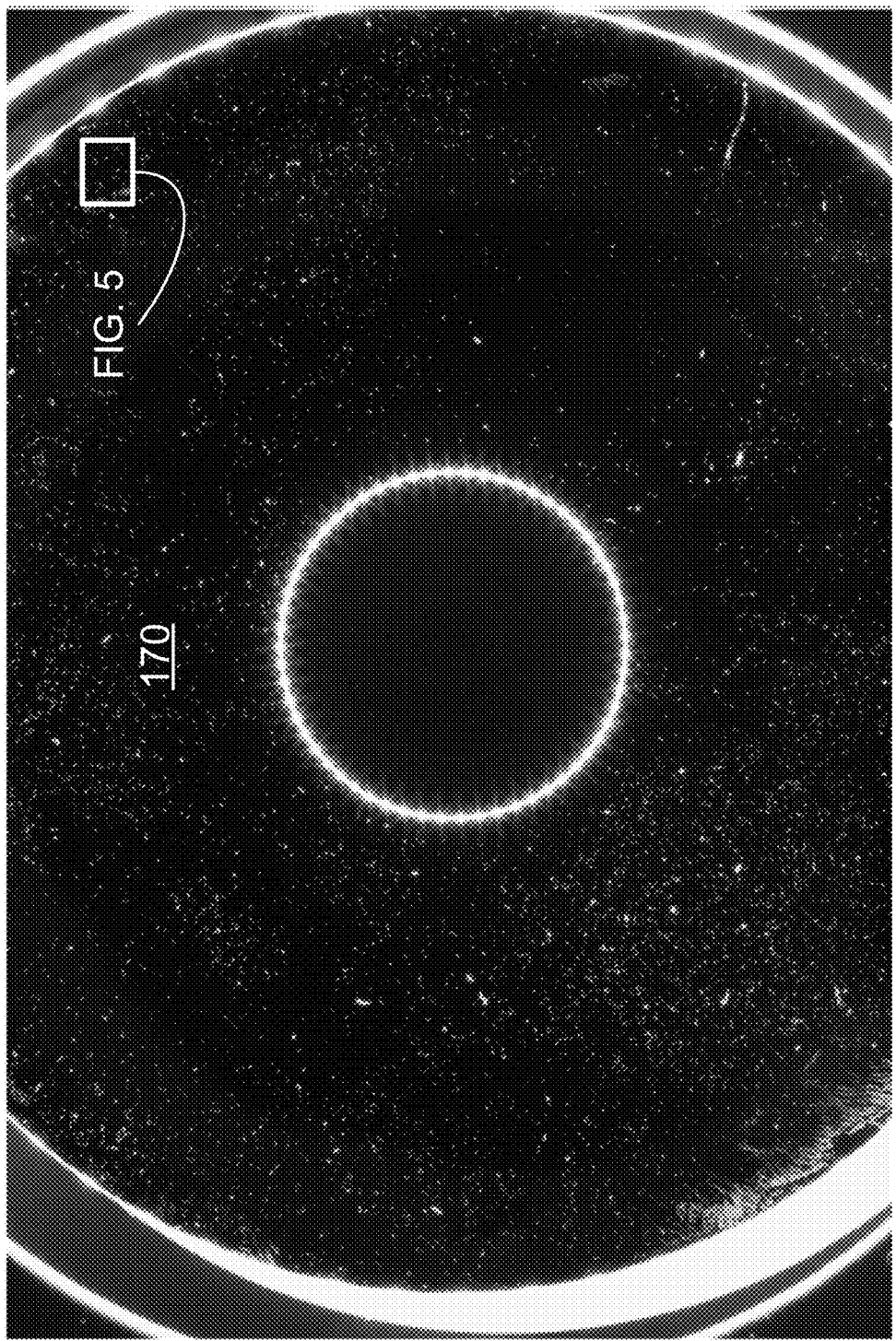

FIG. 4 provides an image of a surface features map of an article according to one aspect of the present embodiments.

FIG. 5 provides a close-up image of a surface features map of an article according to one aspect of the present embodiments.

FIG. 6A (top) provides a close-up image of a surface feature from a surface features map, and FIG. 6A (bottom) provides a photon scattering intensity distribution of the surface feature, according to aspects of the present embodiments.

FIG. 6B (top) provides a close-up, pixel-interpolated image of a surface feature from a surface features map, and FIG. 6B (bottom) provides a photon scattering intensity distribution of the pixel-interpolated surface feature, according to aspects of the present embodiments.

Figure 7A:
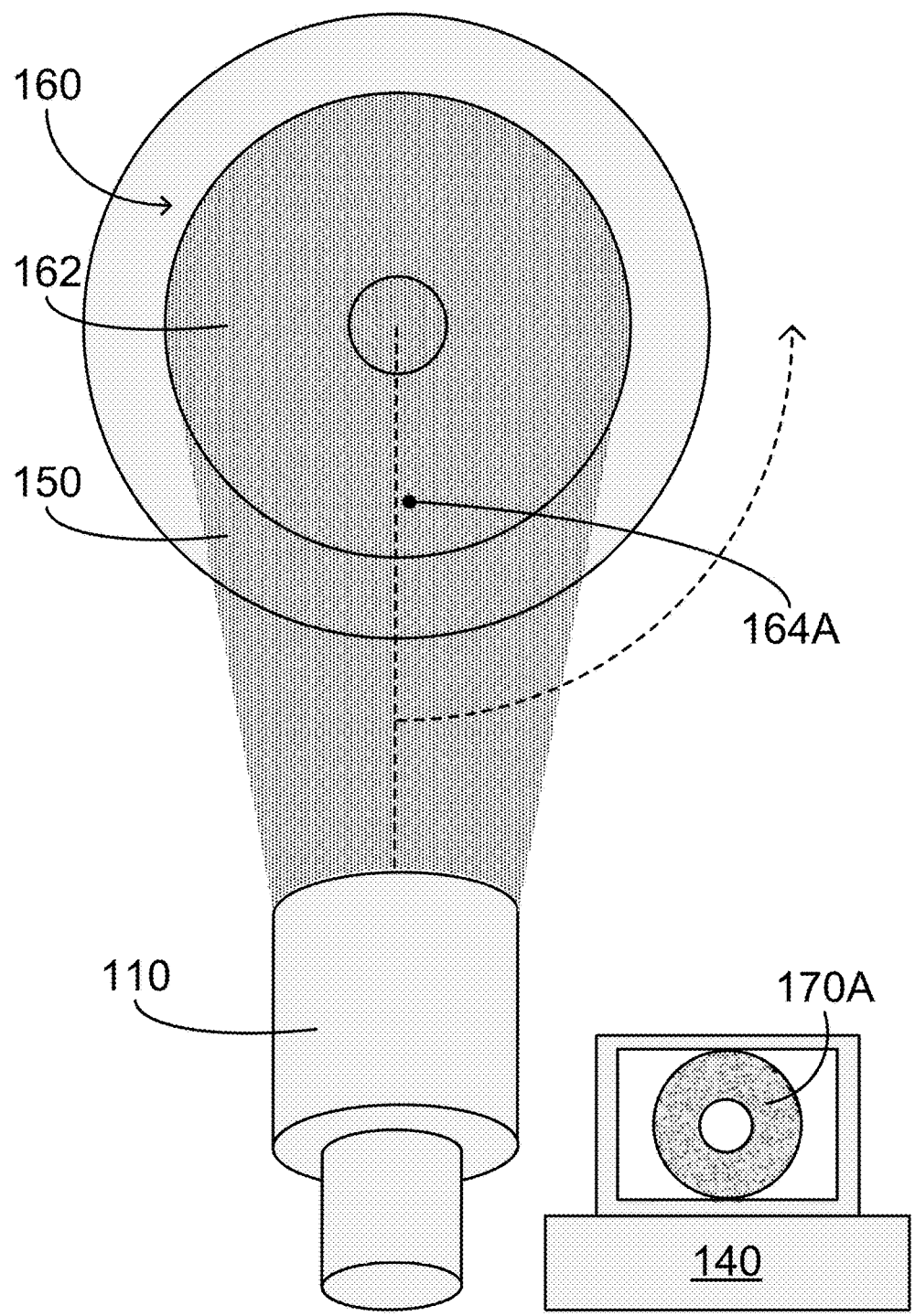

FIG. 7A provides a schematic illustrating detection of surface features of articles at a first azimuthal angle according to one aspect of the present embodiments.

Figure 7B:
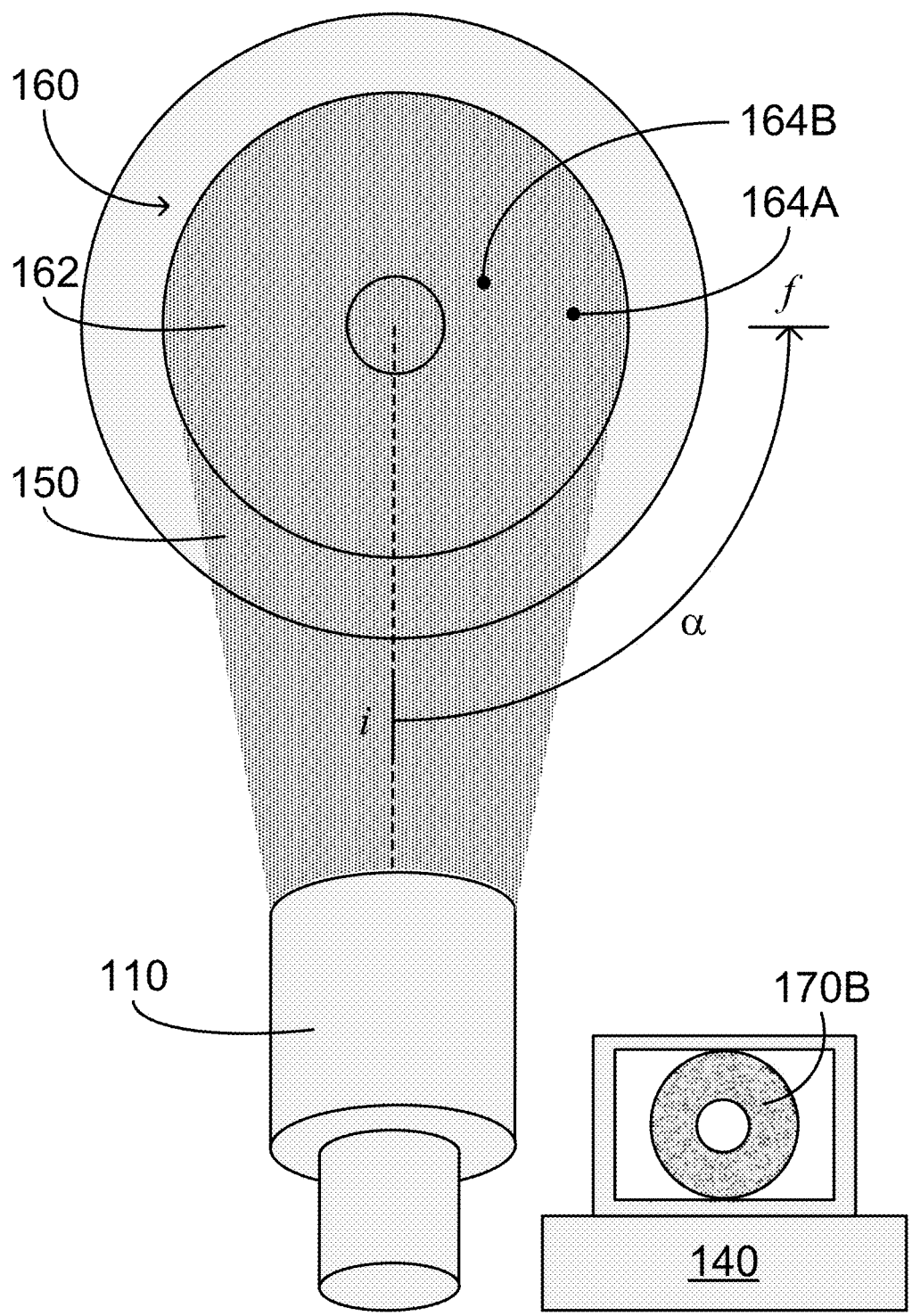

FIG. 7B provides a schematic illustrating detection of surface features of articles at a second azimuthal angle according to one aspect of the present embodiments.

Figure 7C:
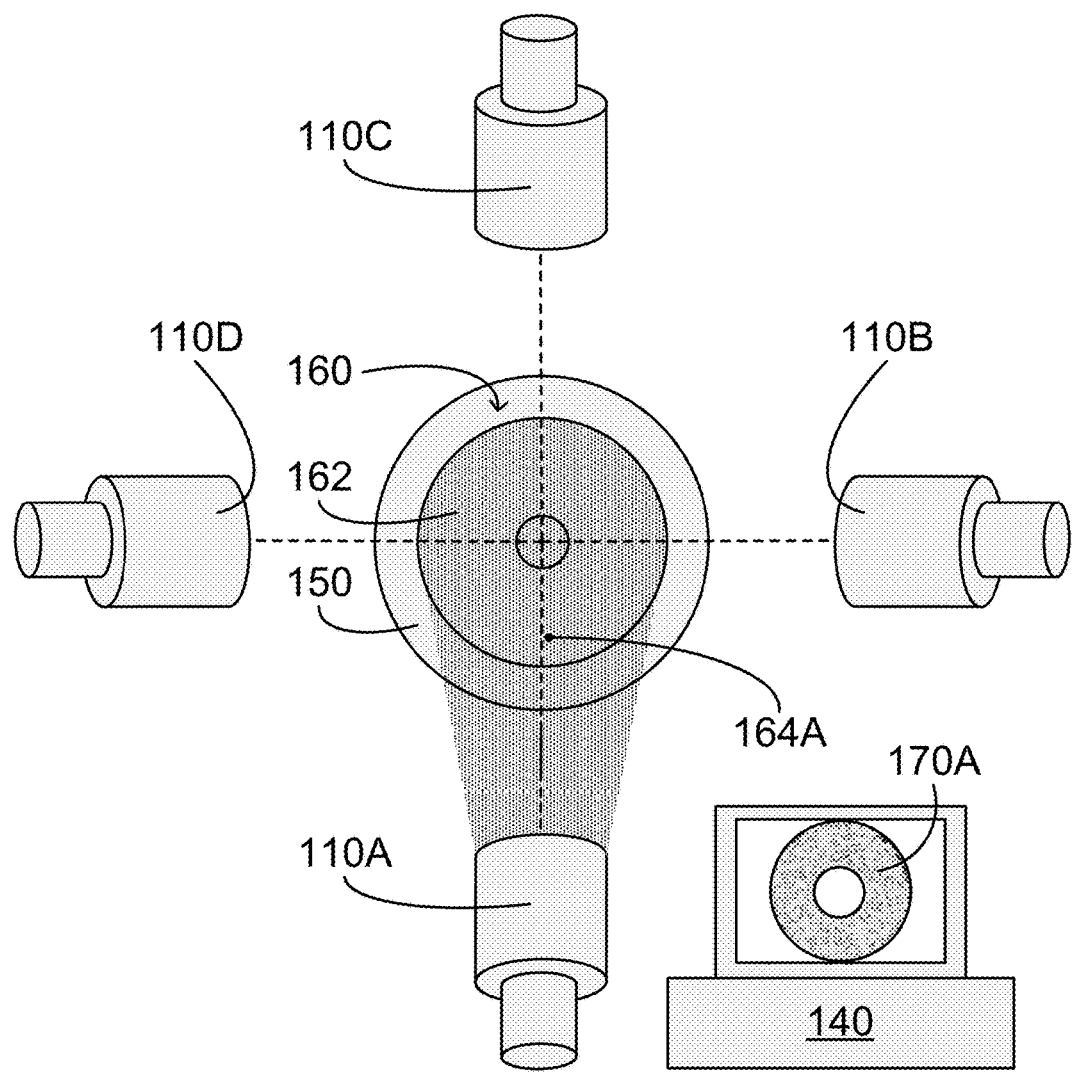

FIG. 7C provides a schematic illustrating detection of surface features of articles at a first azimuthal angle according to one aspect of the present embodiments.

Figure 7D:
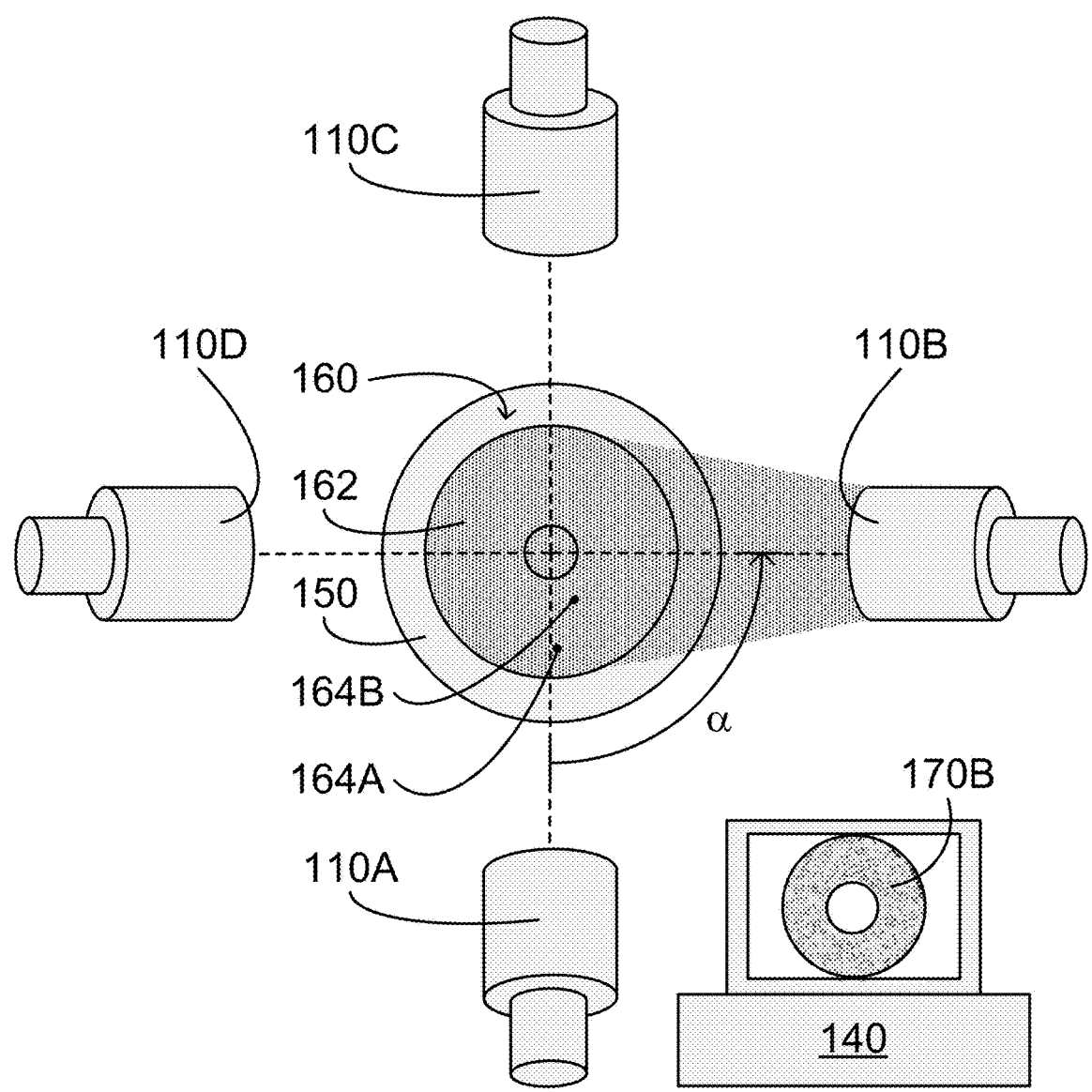

FIG. 7D provides a schematic illustrating detection of surface features of articles at a second azimuthal angle according to one aspect of the present embodiments.

FIG. 8A provides an image of a surface features map of an article at a first azimuthal angle according to one aspect of the present embodiments.

FIG. 8B provides an image of a surface features map of an article at a second azimuthal angle according to one aspect of the present embodiments.

DESCRIPTION

Before some particular embodiments are described and/or illustrated in greater detail, it should be understood by persons having ordinary skill in the art that the particular embodiments provided herein do not limit the concepts provided herein, as elements in such particular embodiments may vary. It should likewise be understood that a particular embodiment provided herein has elements which may be readily separated from the particular embodiment and optionally combined with or substituted for elements in any of several other embodiments described and/or illustrated herein.

It should also be understood by persons having ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

An article fabricated on a production line may be inspected for certain features, including defects that might degrade the performance of the article or a system including the article. For example, a hard disk for a hard disk drive may be fabricated on a production line and inspected for certain surface features, including surface and subsurface defects that might degrade the performance of the disk or the hard disk drive. Provided herein are apparatuses and methods for inspecting articles to detect, map, and/or characterize certain surface features such as surface and/or subsurface defects.

With respect to articles that may be inspected with apparatuses and methods herein, such articles include any article of manufacture or a workpiece thereof in any stage of manufacture having one or more surfaces (e.g., one or more optically smooth surfaces), examples of which include, but are not limited to, semiconductor wafers, magnetic recording media (e.g., hard disks for hard disk drives), and workpieces thereof in any stage of manufacture, including transparent articles such as glass blanks for magnetic recording media. Such articles may be inspected for certain surface features, including surface and/or subsurface defects that might degrade the performance of the article, which surface and/or subsurface defects include particle and stain contamination, as well as defects including scratches and voids. With respect to particle contamination, for example, particles trapped on a surface of an intermediate hard disk (i.e., workpiece) for a hard disk drive may damage subsequently sputtered films. Particle contamination may also contaminate a finished surface of a hard disk drive, leading to scratch formation, debris generation, and corruption of the spacing between the hard disk and the read-write head. As such, it is important to inspect articles with apparatus and methods herein to correct manufacturing trends leading to surface and/or subsurface defects and to increase product quality.

FIG. 1A provides a basis from which to begin a description of features of the apparatuses and methods provided herein. In view of the foregoing, FIG. 1A provides a non-limiting schematic for detecting, mapping, and/or characterizing surface features of articles illustrating an apparatus 100 including a photon emitter 110, an optical setup 120 including an optical component, a photon detector array 130, a computer or equivalent device 140, an optional stage 150 configured to support an article 160 and/or rotate an article 160 through a number of azimuthal angles, and a surface features map 170 of a surface of the article 160. As such, FIG. 1A provides a basis from which to begin a description of photon emitters, optical components of the optical setup, photon detector arrays, etc. The apparatuses and methods provided herein are not limited to FIG. 1A, as additional embodiments are provided herein, and additional embodiments may be realized by the features provided in more detail herein.

An apparatus may include a single photon emitter (e.g., see photon emitter 110 of FIG. 1A) or a number of photon emitters (e.g., see photon emitters 110A-C of FIGS. 7C and 7D). In some embodiments, for example, the apparatus may include at least 1, 2, 3, 4, 5, 6, 7, 8, 9, or 10 photon emitter(s). In some embodiments, for example, the apparatus may include no more than 10, 9, 8, 7, 6, 5, 4, 3, 2, or 1 photon emitter(s). Combinations of the foregoing may also be used to describe the number of photon emitters of the apparatus. In some embodiments, for example, the apparatus may include at least 2 photon emitters and no more than 10 photon emitters (e.g., between 2 and 10 photon emitters), such as at least 2 photon emitters and no more than 6 photon emitters (e.g., between 2 and 6 photon emitters), including at least 2 photon emitters and no more than 4 photon emitters (e.g., between 2 and 4 photon emitters). A single photon emitter may be used to emit photons onto a surface of an article, such as the entire surface of the article or some predetermined portion of the surface of the article (e.g., for gradational rotation of the article for piecewise inspection, if desired); each photon emitter of a number of photon emitters may be used to emit photons onto the surface of the article, such as the entire surface of the article or some predetermined portion of the surface of the article, at different times and/or at the same time in any collection of photon emitters (e.g., see photon emitters 110A-C of FIGS. 7C and 7D). Further with respect to the number of photon emitters, each photon emitter of a number of photon emitters may be the same or different, or some combination thereof (e.g., at least 2 of the same photon emitter, with the remainder of photon emitters being different; at least 4 of the same photon emitter, with the remainder of photon emitters being different; etc.). In some embodiments, for example, the apparatus may include at least two different photon emitters, wherein the two different photon emitters are each separately configured to emit photons onto a surface of an article, such as the entire surface of the article or some predetermined portion of the surface of the article.

Whether the apparatus includes a single photon emitter or a number of photon emitters, each photon emitter may emit photons onto a surface of an article at one or more distances and/or angles optimized for one or more types of features, which types of features are described in more detail herein. One angle may be equal to the glancing angle, which is the complement of the angle of incidence, and which angle of incidence is the angle between a ray including the emitted photons incident on the surface of the article and the normal (e.g., a line or vector perpendicular to the surface of the article) at the point at which the ray is incident. The glancing angle may also be described as an altitudinal angle or the smallest angle between a ray including the emitted photons incident on the surface of the article and the surface at the point at which the ray is incident. Another angle optimized for one or more types of features may be equal to the azimuthal angle, which is described in more detail herein.

FIG. 2 provides a number of rays including emitted photons incident on a surface 162 of an article 160 that form a glancing angle with the surface 162. FIG. 2 further provides a number of rays including reflected photons that form an angle of reflection with the normal to the surface, which angle of reflection is equal in magnitude to the angle of incidence. FIG. 2 even further provides a number of rays including scattered photons from a feature 164 on the surface 162 of the article 160, which rays including scattered photons form various scatter angles. A photon emitter may emit photons at a glancing angle ranging from 0° to 90°, wherein a glancing angle of 0° represents the photon emitter emitting photons onto the surface of the article from a side of the article, and wherein a glancing angle of 90° represents the photon emitter emitting photons onto the surface of the article from directly above the article. In some embodiments, for example, a photon emitter may emit photons onto a surface of an article such that the glancing angle is at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon emitter may emit photons onto a surface of an article such that the glancing angle is no more than 90°, 85°, 80°, 75°, 70°, 65°, 60°, 55°, 50°, 45°, 40°, 35°, 30°, 25°, 20°, 15°, 10°, 5°, or 0°. Combinations of the foregoing may also be used to describe the glancing angle at which a photon emitter may emit photons onto a surface of an article. In some embodiments, for example, a photon emitter may emit photons onto a surface of an article such that the glancing angle is at least a 0° and no more than 90° (i.e., between 0° and 90°), such as at least 0° and no more than 45° (i.e., between 0° and 45°), including at least 45° and no more than 90° (i.e., between 45° and 90°).

A photon emitter may emit photons onto a surface of an article, such as the entire surface or some predetermined portion of the surface (e.g., for gradational rotation of the article for piecewise inspection, if desired). The photon emitter may further emit photons onto the entire surface of the article or some predetermined portion of the surface such that the entire surface or the predetermined portion of the surface is uniformly or homogenously illuminated. Uniformly illuminating the entire surface of the article or some predetermined portion of the surface includes, but is not limited to, subjecting the entire surface of the article or some predetermined portion of the surface of the article to the same or about the same quantity of photons per unit time (e.g., photon flux), the same or about the same photon energy per unit time (e.g., photon power), and/or the same or about the same photon power per unit area (e.g., photon power density or photon flux density). In radiometric terms, uniformly illuminating includes, but is not limited to, subjecting the entire surface of the article or some predetermined portion of the surface of the article to the same or about the same quantity of light per unit time, the same or about the same radiant energy per unit time (e.g., radiant power or radiant flux), and/or the same or about the same radiant power per unit area (e.g., irradiance or radiant flux density).

With the appreciation that photons are the elementary particles of electromagnetic radiation or light, a photon emitter or light source may provide light including a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light including a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. A photon emitter or light source may be used in conjunction with one or more optical components of an optical setup to provide light having any of the foregoing qualities. Wavelength filters, for example, may be used in conjunction with a photon emitter or light source to provide light including a relatively wide range of wavelengths or frequencies, a relatively narrow range of wavelengths or frequencies, or a particular wavelength or frequency. Polarization filters, for example, may also be used in conjunction with a photon emitter or light source to provide light of a desired polarization including polarized light, partially polarized light, or nonpolarized light.

In view of the foregoing, a photon emitter or light source may include a lamp such as a flash lamp, including a high-speed flash lamp, configured to minimize vibration while detecting photons scattered from surface features of an article with a photon detector array. In some embodiments, for example, a photon emitter or light source may include a high-speed Xe flash lamp such as a 500 W Xe flash lamp to minimize vibration while detecting photons scattered from surface features of an article with a photon detector array.

Also in view of the foregoing, a photon emitter or light source may include a collimated light source such as a laser, including a combination of lasers, configured to emit photons onto a surface of an article at one or more angles. In some embodiments, for example, a combination of lasers may be provided to a laser beam shaper such that the combination of lasers emits photons onto a surface of an article at one angle. In some embodiments, for example, a combination of lasers may be provided to a laser beam shaper such that the combination of lasers emits photons onto a surface of an article at multiple angles. In some embodiments, for example, at least 2, 4, 6, 8, 10, 12, 14, 16, 18, 20, 22, 24, 26, 28, or 30 lasers, or even more than 30 lasers, may be provided to a laser beam shaper such that the combination of lasers emits photons onto a surface of an article at one or more angles. In some embodiments, for example, no more than 30, 28, 26, 24, 22, 20, 18, 16, 14, 12, 10, 8, 6, 4, or 2 lasers may be provided to a laser beam shaper such that the combination of lasers emits photons onto a surface of an article at one or more angles. Combinations of the foregoing may also be used to describe combinations of lasers provided to a laser beam shaper. In some embodiments, for example, at least 2 lasers and no more than 30 lasers (e.g., between 2 and 30 lasers), such as at least 10 lasers and no more than 30 lasers (e.g., between 10 and 30 lasers), including at least 20 lasers and no more than 30 lasers (e.g., between 20 and 30 lasers), and further including at least 24 lasers and no more than 28 lasers (e.g., between 24 and 28 lasers) may be provided to a laser beam shaper such that the combination of lasers emits photons onto a surface of an article of an article at one or more angles.

Further in view of the foregoing, a photon emitter or light source may include a two-dimensional light source such as a combination of point light sources, including a linear combination or array, an arcuate combination or array, etc. of point light sources configured to emit photons onto a surface of an article. In some embodiments, for example, a two-dimensional light source may include a combination of at least 10, 20, 40, 60, 80, 100, 110, 120, 140, 160, 180, or 200 point light sources, or even more than 200 point sources. In some embodiments, for example, a two-dimensional light source may include a combination of no more than 200, 180, 160, 140, 120, 100, 80, 60, 40, 20, or 10 point light sources. Combinations of the foregoing may also be used to describe two-dimensional light sources including combinations of point light sources. In some embodiments, for example, a two-dimensional light source may include a combination of at least 10 and no more than 200 (e.g., between 10 and 200) point light sources, such as at least 40 and no more than 160 (e.g., between 40 and 160) point light sources, including at least 60 and no more than 140 (e.g., between 60 and 140) point light sources, and further including at least 80 and no more than 120 (e.g., between 80 and 120) point light sources. Such point light sources may be combined in rows and columns of a two-dimensional array, including linearly combined to form a two-dimensional light source such as a strip light. Such point light sources may be arcuately combined to form a two-dimensional light source such as a ring light. In some embodiments, for example, a photon emitter or light source may include a two-dimensional light source including at least 60 point light sources, such as a ring light including at least 60 point light sources, including a ring light including at least 60 light-emitting diodes ("LEDs"), and further including a ring light including at least 100 LEDs. A two-dimensional light source including LEDs may include white LEDs, wherein each LED has a power of at least 10 mW. An LED-based ring light may enhance features such as scratches (e.g., circumferential scratches) and/or voids in surfaces of articles, especially when the LED-based ring light is configured to emit photons onto the surfaces of the articles with lower angles (e.g., glancing angle equal to or less than 45°).

The apparatus may further include an optical setup (e.g., optical setup including one or more of optical components 120 of FIG. 1A), which optical setup may manipulate photons emitted from one or more photon emitters, photons reflected from a surface of an article, and/or photons scattered from surface features of an article. With the appreciation that photons are the elementary particles of electromagnetic radiation or light, the optical setup may manipulate light emitted from one or more photon emitters, light reflected from a surface of an article, and/or light scattered from surface features of an article. The optical setup up may include any of a number of optical components positioned before the article such that the optical components may be used to manipulate photons emitted from one or more photon emitters before uniformly or homogenously illuminating the entire surface or the predetermined portion of the surface of the article. Alternatively, or in addition, the optical setup up may include any of a number of optical components positioned after the article such that the optical components may be used to manipulate photons reflected from the surface of the article or scattered from surface features of the article. Alternatively, or in addition, an optical component including the article (e.g., article 160 of FIG. 1A) may be used to manipulate (e.g., reflect) photons. The forgoing optical components may include, but are not limited to, optical components such as lenses, filters, gratings, and mirrors, which mirrors include articles having optically smooth surfaces.

With respect to optical components such as lenses, the optical setup may include a single lens or a number of lenses, including, but not limited to, a combination of a lens coupled to a photon detector array (e.g., a lens-and-photon-detector-array combination including lens 120 and photon detector array 130 of FIG. 1A) configured for collecting and detecting photons scattered from surface features of articles. The lens coupled to the photon detector array may have an entrance pupil and an exit pupil, and additional optical components such as lenses (e.g., lenses in addition to the lens coupled to the photon detector array), filters, gratings, and mirrors, may be positioned in any combination of one or more optical components at or near the entrance pupil of the lens coupled to the photon detector array, at or near the exit pupil of the lens coupled to the photon detector array (i.e., in-between the exit pupil of the lens and the photon detector array), or some combination thereof to manipulate photons scattered from surface features of articles. The lens coupled to the photon detector array may be an objective lens, such as a telecentric lens, including an object-space telecentric lens (i.e., entrance pupil at infinity), an image-space telecentric lens (i.e., exit pupil at infinity), or a double telecentric lens (i.e., both pupils at infinity). Coupling a telecentric lens to a photon detector array reduces errors with respect to the position of surface features of articles, reduces distortion of surface features of articles, enables quantitative analysis of photons scattered from surface features of articles, which quantitative analysis includes integration of photon scattering intensity distribution for size determination of surface features of articles.

With respect to optical components such as filters, the optical setup may include a filter or a number of filters including, but not limited to, one or more wavelength filters, band-pass filters, polarization filters, coherence filters, periodic array-tuned filters, and phase filters. As described herein, when one or more of such filters is positioned before an article to manipulate photons emitted from a photon emitter, photons/light having any of a number of different qualities may be provided to a surface of the article. When one or more of such filters is positioned after an article to manipulate photons scattered from surface features of the article, the one or more filters may be used for distinguishing between surface features of the article. For example, a wavelength filter may be used to distinguish between surface features known to differentially scatter photons with respect to wavelength; a polarization filter may be used to distinguish between surface features known to differentially scatter photons with respect to polarization; a coherence filter may be used to distinguish between surface features known to differentially scatter photons with respect to coherence; and a phase filter or waveplate may be used to distinguish between surface features known to differentially scatter photons with respect to phase. In some embodiments, for example, an optical component such as a filter may be positioned at or near the entrance pupil of a lens (e.g., telecentric lens) coupled to a photon detector array. In some embodiments, for example, an optical component such as a filter may be positioned at or near the exit pupil of a lens (e.g., telecentric lens) coupled to a photon detector array.

With respect to optical components including reflective surfaces such as mirrors, the optical setup may include one or more mirrors of any curvature including, but not limited to, one or more mirrors selected from optical-grade mirrors and one-way mirrors, including articles including optically smooth surfaces. The one or more mirrors may be positioned about an apparatus to manipulate photons emitted from one or more photon emitters, reflected from a surface of an article, scattered from surface features of an article, or combinations thereof. As such, the one or more mirrors may be positioned in a light path before an article (e.g., a one-way mirror between a photon emitter and the article); in the light path after an article; in the light path under an article, for example, parallelly proximate to a transparent article; or in combinations thereof. In some embodiments, for example, one or more mirrors may be used to redirect photons reflected off a surface of an article back onto the surface of the article, thereby recycling photons that would otherwise be lost to the environment.

To detect photons scattered from surface features of articles, an apparatus may further include a single photon detector array (e.g., see photon detector array 130 of FIG. 1A) including a number of photon detectors or a number of photon detector arrays, each including a number of photon detectors. In some embodiments, for example, the number of photon detector arrays may include at least 2, 3, 4, 5, 6, 7, 8, 9, or 10 photon detector arrays (For example, FIG. 1B shows two photon detectors 130A and 130B with two optical components 120A and 120B). In some embodiments, for example, the number of photon detector arrays may include no more than 10, 9, 8, 7, 6, 5, 4, 3, or 2 photon detector arrays. Combinations of the foregoing may also be used to describe the number of photon detector arrays. In some embodiments, for example, the number of photon detector arrays may include at least 2 photon detector arrays and no more than 10 photon detector arrays (e.g., between 2 and 10 photon detector arrays), such as at least 2 photon detector arrays and no more than 5 photon detector arrays (e.g., between 2 and 5 photon detector arrays). Further with respect to the number of photon detector arrays, each photon detector array of the number of photon detector arrays may be the same or different, or some combination thereof (e.g., at least 2 of the same photon detector array, with the remainder of photon detector arrays being different; at least 3 of the same photon detector array, with the remainder of photon detector arrays being different; etc.).

Whether the apparatus includes a single photon detector array or a number of photon detector arrays, each photon detector array may be oriented to detect photons scattered from surface features of an article at one or more distances and/or angles for an optimum acceptance of photons (e.g., maximum acceptance of photons with minimum background noise) scattered from one or more types of features, which types of features are described in more detail herein. Likewise, a lens-and-photon-detector-array combination may be oriented to collect and detect photons scattered from surface features of an article at one or more distances and/or angles for an optimum acceptance of photons scattered from one or more types of features. One angle may be the angle between a ray including the center line axis of the lens and/or the photon detector array extended to the surface of the article and the normal (e.g., a line or vector perpendicular to the surface of the article) at the point at which the ray is extended. The angle, optionally in combination with an aperture that may be optimally sized for maximum acceptance of scattered photons with minimum background noise, or optionally in combination with an aperture that may be variably sized, such as more widely sized or more narrowly sized to respectively accept a wider range or narrower range of scattered photons, may be oriented to allow for acceptance of scattered photons having a number of scatter angles, which scattered photons may be scattered from one or more types of features. A scatter angle may be different than the angle of reflection, which angle of reflection is equal in magnitude to the angle of incidence as described herein. FIG. 2 provides a number of rays including photons scattered from a feature 164 on a surface 162 of an article 160, which rays represent various scatter angles.

In view of the foregoing, the angle at which a photon detector array or lens-and-photon-detector-array combination may be oriented ranges from 0° to 90°, inclusive, wherein an angle of 0° represents orientation of the photon detector array or the lens-and-photon-detector-array combination directly above the article, and wherein an angle of 90° represents orientation of the photon detector array or lens-and-photon-detector-array combination at a side of an article. In some embodiments, for example, a photon detector array or lens-and-photon-detector-array combination may be oriented at an angle of at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon detector array or lens-and-photon-detector-array combination may be oriented at an angle of no more than 90°, 85°, 80°, 75°, 70°, 65°, 60°, 55°, 50°, 45°, 40°, 35°, 30°, 25°, 20°, 15°, 10°, or 5°, or 0°. Combinations of the foregoing may also be used to describe the angle at which the photon detector array or lens-and-photon-detector-array combination may be oriented. In some embodiments, for example, a photon detector array or lens-and-photon-detector-array combination may be oriented at an angle of at least a 0° and no more than a 90° (i.e., between 0° and 90°), such as least 0° and no more than 45° (i.e., between 0° and 45°) or at least 45° and no more than 90° (i.e., between 45° and 90°).

The photon detector array, optionally in combination with a lens (e.g., telecentric lens), may detect photons scattered from surface features of an article, such as the entire surface of the article or some predetermined portion of the surface of the article. The photon detector array, optionally in combination with a lens (e.g., telecentric lens), may detect photons scattered from surface features of an article, such as the entire surface of the article or some predetermined portion of the surface of the article, while oriented at a distance and/or an angle for an optimum acceptance of photons (e.g., maximum acceptance of photons with minimum background noise) scattered from one or more types of features. As provided herein, the angle for an optimum acceptance of photons scattered from one or more types of features may allow for acceptance of scattered photons respectively having a number of scatter angles, which scattered photons may respectively be scattered from one or more types of features.

With the appreciation that photons are the elementary particles of electromagnetic radiation or light, a photon detector array or light detector array may detect light including a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light including a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon detector array or light detector array may be used in conjunction with one or more optical components of an optical setup to detect light having any of the foregoing qualities.

The photon detector array may include a number of pixel sensors, which pixel sensors, in turn, may each include a photon detector (e.g., a photodiode) coupled to a circuit including a transistor configured for amplification. Features of a photon detector array including such pixel sensors include, but are not limited to, low temperature operation (e.g., down to −40° C.), low electron noise (e.g., 2-10 e-RMS; 1 e-RMS; <1 e-RMS; etc.), wide dynamic range (e.g., 30,000:1, 8,500:1; 3,000:1; etc.), and/or decreased photon/light collection time. A photon detector array may include a large number of pixel sensors (e.g., ≥1,000,000 or ≥1M pixel sensors) arranged in rows and columns of a two-dimensional array, wherein each pixel sensor includes a photon detector coupled to an amplifier. In some embodiments, for example, a photon detector array may include at least 1M, 2M, 3M, 4M, 5M, 6M, 7M, 8M, 9M, 10M, or more, pixel sensors arranged in rows and columns of a two-dimensional array. In some embodiments, for example, a photon detector array may include no more than 10M, 9M, 8M, 7M, 6M, 5M, 4M, 3M, 2M, or 1M, pixel sensors arranged in rows and columns of a two-dimensional array. Combinations of the foregoing may also be used to describe the number of pixel sensors in a photon detector array. In some embodiments, for example, a photon detector array may include at least 1M and no more than 10M (e.g., between 1M and 10M) pixel sensors arranged in rows and columns of a two-dimensional array, such as at least 1M and no more than 8M (e.g., between 1M and 8M) pixel sensors, including at least 1M and no more than 6M (e.g., between 1M and 6M) pixel sensors, further including at least 2M and no more than 6M (e.g., between 1M and 6M) pixel sensors, and even further including at least 2M and no more than 5M (e.g., between 2M and 5M) pixel sensors.

Due to surface reflections of surface features of articles and/or small angle scattering (e.g., 4π scattering), surface features may appear much larger in size enabling pixel sensors larger the than surface features to be used. In some embodiments, for example, a photon detector array may include micrometer-sized (i.e., admits of µm units as measured) pixel sensors at least 1 µm, 2 µm, 3 µm, 4 µm, 5 µm, 6 µm, 7 µm, 8 µm, 9 µm, or 10 µm in their smallest dimension. In some embodiments, for example, a photon detector array may include micrometer-sized pixel sensors no more than 10 µm, 9 µm, 8 µm, 7 µm, 6 µm, 5 µm, 4 µm, 3 µm, 2 µm, or 1 µm in their smallest dimension. Combinations of the foregoing may also be used to describe dimensions of micrometer-sized pixel sensors in photon detector arrays. In some embodiments, for example, a photon detector array may include micrometer-sized pixel sensors at least 1 µm and no more than 10 µm (e.g., between 1 µm and 10 µm) in their smallest dimension, such as at least 1 µm and no more than 7 µm (e.g., between 1 µm and 7 µm), including at least 4 µm and no more than 10 µm (e.g., between 4 µm and 10 µm), and further including at least 4 µm and no more than 7 µm (e.g., between 4 µm and 7 µm). Such micrometer-sized pixel sensors may be used in the apparatus for detecting, mapping, and/or characterizing surface features of articles, wherein the surface features are more than 100 times smaller than the micrometer-sized pixel sensors.

In view of the foregoing, the single photon detector array or the number of photon detector arrays may each include a complementary metal-oxide semiconductor ("CMOS") or a scientific complementary metal-oxide semiconductor ("sCMOS"), each of which may optionally be part of CMOS camera or a sCMOS camera, respectively. Alternatively, the single photon detector array or the number of photon detector arrays may each include a charge-coupled device ("CCD"), which may optionally be part of CCD camera. While a CCD-based photon detector array might have a slower recording speed than a CMOS-based or sCMOS-based photon detector array, a CCD-based photon detector array may be desirable in applications requiring less electronic and/or image noise. A CCD-based photon detector array, including an electron-multiplying CCD ("EMCCD"), may also be desirable in certain applications having low-light conditions. Furthermore, a number of photon detector arrays is not limited to combinations of either CMOS/sCMOS-based photon detector arrays or CCD-based photon-detector arrays, as a number of photon detector arrays may include a combination of any of a number of CMOS/sCMOS-based photon detector arrays and CCD-based photon-detector arrays in applications that benefit from employing each type of technology. In some embodiments, for example, a CMOS/sCMOS-based photon detector array may be used to detect photons scattered from surface features of articles in certain applications having sufficient light for the CMOS/sCMOS-based photon detector array, while a CCD/EMCCD-based photon detector array may be used to detect photons scattered from surface features of articles in certain applications having too little light for the CMOS/sCMOS-based photon detector array.

FIG. 3 provides a schematic for detection of surface features of an article, illustrating a close-up, cross-sectional view of an apparatus including an optical setup and a photon detector array. As shown, article 160 includes a surface 162 and one or more surface features such as surface feature 164. Photons may be scattered by the surface features and collected and detected by a combination including a lens 120 coupled to a photon detector array 130, which combination may be positioned at a distance and/or an angle for an optimum acceptance of photons (e.g., maximum acceptance of photons with minimum background noise) scattered from one or more types of features. The optical setup, which may include a telecentric lens (e.g., lens 120 of FIG. 1A), may collect and focus the photons scattered from one or more surface features onto one or more pixel sensors 132 of photon detector array 130, which one or more pixel sensors may each include a photon detector coupled to an amplifier (e.g., CMOS/sCMOS-based photon detector array; EMCCD-based photon detector array; etc.). The one or more pixel sensors 132, each of which may correspond to a particular, fixed area of an article's surface and a pixel in a map of the article's surface, may provide one or more signals to a computer or equivalent device for mapping an article's surface or otherwise determining the position of one or more features on the article's surface. FIG. 4 provides an image of such a surface features map, FIG. 5 provides a close-up image of such a surface features map (e.g., a close-up image of the surface features map of FIG. 4), and FIG. 6A further provides a close-up image of such a surface features map (e.g., a close-up image of the surface features map of FIG. 5), wherein the close-up image of FIG. 6A is centered about a single surface features such as surface feature 164. The computer or equivalent device may subsequently use pixel interpolation for further mapping surface features such as surface feature 164 as provided in FIG. 6B.

Depending upon factors that may include the type of article, the type of surface features (e.g., particle, stain, scratch, void, etc.), and the like, it may be desirable at times to increase detection time of a single photon detector array or a number of photon detector arrays to detect more photons for detecting, mapping, and/or characterizing surface features of articles. In some embodiments, for example, detection time of a single photon detector array or a number of photon detector arrays may be increased to detect more photons. In such embodiments, a CCD-based photon detector array, including an electron-multiplying EMCCD may be used to further detect more photons. Alternately, or in addition, it may be desirable to increase the number of photons (e.g., photon energy) emitted from a single photon emitter or a number of photon emitters to provide an increase in photons scattered for detecting, mapping, and/or characterizing surface features of articles. Such an increase in photon energy may be with respect to unit time for increased photon power, or with respect to unit area for increased photon flux density. Alternately to one or both of increasing the photon energy or detection time, or in addition to increasing the photon energy and detection time, it may be desirable at times to minimize background noise including stray light from one or more photon emitters, background light, and/or background fluorescent radiation.

The apparatus may further include one or more computers or equivalent devices (e.g., devices that include primary and/or secondary memory and one or more processing elements operable to carry out arithmetic and logical operations), including, but not limited to, servers, workstations, desktop computers, nettops, laptops, netbooks, and mobile devices such as tablets and smartphones, which computers or equivalent devices may contain graphics processing units ("GPU"s), application-specific integrated circuits ("ASIC"s), field-programmable gate arrays ("FPGA"s), etc. The computers or equivalent devices may include a computer-readable storage medium for instructions making the apparatus operable to, but not limited to, convey each article to the apparatus for inspection; position each article for inspection, optionally including gradational or continuous rotation of the article for detecting, mapping, and/or characterizing surface features from different azimuthal angles; hold or otherwise maintain the position of each article for inspection; insert optical components into the optical setup, for example, using a mechanical actuator; position optical components for inspection; adjust optical components (e.g., focus lenses) and/or tune optical components (e.g., piezoelectric-based wavelength filters; piezoelectric-based polarization filters; etc.) for inspection; remove optical components from the optical setup; move each photon emitter into position for inspection, wherein the position for inspection may include a photon emitter-article distance and/or angle (e.g., glancing angle) optimized for one or more types of features; switch each photon emitter on and off, or otherwise between modes for emitting photons and not emitting photons; move each photon detector array into position for inspection, wherein the position for inspection may include a photon detector array-article distance and/or angle (e.g., scatter angle) optimized for one or more types of features; switch each photon detector array on and off, or otherwise between modes for detecting photons and not detecting photons; synchronize each photon emitter with each photon detector in accordance with a photon emission-photon detection scheme; process photon detector array signals from scattered photons, optionally including pixel interpolation for better accuracy (e.g., 10× better than pixel size) with respect to the position of surface features; map or otherwise determine the position of surface features of articles from photon detector array signals or processed photon detector array signals (e.g., photon scattering intensity distributions); quantitatively and/or qualitatively characterize surface features of articles; catalog surface features of articles; and determine trends with respect to surface features of articles.

The morphology, form, or shape of one or more surface features of articles, including one or more surface and/or subsurface defects, may affect the way in which the one or more surface features scatter photons, an effect that may occur when photons are emitted onto a surface of an article from a single azimuthal angle. For example, a surface feature including an oxide may have a faceted surface that scatters photons in a way that is not optimally detected or not detected at all by a photon detector array when photons are emitted onto a surface of an article from a single azimuthal angle. In view of the foregoing, an apparatus in which photons are emitted onto a surface of an article at a number of azimuthal angles may improve detection of photons scattered from surface features of articles by flushing out rotational dependencies, which, in turn, may result in optimal detection of surface features and/or increased detection of surface features, thereby increasing the sensitivity of the apparatus and/or certainty that as many of the surface features as possible are detected.

As provided herein, FIG. 1A provides a non-limiting schematic for detecting, mapping, and/or characterizing surface features of articles illustrating an apparatus 100. The apparatus 100 may include a photon emitter 110, an optical setup 120 including an optical component, a photon detector array 130, a computer or equivalent device 140, an optional stage 150 configured to support an article 160 and/or rotate an article 160 through a number of azimuthal angles, and a surface features map 170 of a surface of the article 160, detailed description for the which is also provided herein. Turning to FIGS. 7A-7D, which draw upon FIG. 1A and the detailed description thereof, FIGS. 7A-7D provide non-limiting schematics illustrating detection of surface features of articles at a number of azimuthal angles. FIGS. 7A and 7B, for example, provide non-limiting schematics illustrating detection of surface features of articles at a number of azimuthal angles using a rotatable stage. FIGS. 7C and 7D, for example, provide non-limiting schematics illustrating detection of surface features of articles at a number of azimuthal angles using a number of photon emitters. While presented separately, the concepts presented herein with respect to FIGS. 7A and 7B and the concepts presented herein with respect to FIGS. 7C and 7D may be combined such that the detection of surface features of articles at a number of azimuthal angles may be effected through both a rotatable stage and a number of photon emitters.

Turning to FIGS. 7A and 7B, FIG. 7A provides a non-limiting schematic illustrating detection of surface features of articles at a first azimuthal angle using the stage 150, which stage 150 is configured to rotate. As illustrated, the rotatable stage 150 may rotate the article 160 such that it is azimuthally positioned at the first azimuthal angle for a first surface features map 170A, or for collection of information sufficient to produce the first surface features map 170A. The photon emitter 110 may emit photons onto the surface 162 of the article 160 at the first azimuthal angle, scattering photons from surface features such as surface feature 164A in the process. A photon detector array such as photon detector array 130 of FIG. 1A may then detect photons scattered from the surface features such as the surface feature 164A, photon-detector-array signals from which photon detector array may be used for the first surface features map 170A. FIG. 8A provides an image of such a surface features map 170A at a nominal azimuthal angle of 270°, in which the surface feature 164A is labeled "only 1 defect seen."

FIG. 7B provides a non-limiting schematic illustrating detection of surface features of articles at a second azimuthal angle using the rotatable stage 150. As illustrated, the rotatable stage 150 may rotate the article 160 such that it is azimuthally positioned at the second azimuthal angle for a second surface features map 170B, or for collection of information sufficient to produce the second surface features map 170B. The photon emitter 110 may emit photons onto the surface 162 of the article 160 at the second azimuthal angle, scattering photons from surface features in the process, such as scattering photons from the surface feature 164A, as well as scattering photons from a surface feature 164B. The photon detector array may then detect photons scattered from the surface features such as the surface feature 164A and the surface feature 164B, which surface feature 164B may not have been optimally detected or not detected at all at the first azimuthal angle. As such, by virtue of rotating the article through the azimuthal angle α, surface features such as surface feature 164B are better detected or additionally detected. As with first surface features map 170A, photon-detector-array signals from the photon detector array may be used for the second surface features map 170B. FIG. 8B provides an image of such a surface features map 170B at a nominal azimuthal angle of 240°, in which the surface feature 164A and 164B are labeled "2 defects seen." In view of the combination of surface features maps 170A and 170B providing better information or more information on surface features of articles than any one of surface features maps 170A and 170B, the number of azimuthal angles at which photons are emitted on the surface of the article increases the sensitivity of the apparatus and/or the certainty that as many of the surface features as possible are identified.

The rotatable stage 150 illustrated in FIGS. 7A and 7B may be configured to gradationally rotate or continuously rotate the article 160 respectively for piecewise or continuous detecting, mapping, and/or characterizing surface features. With respect to piecewise detecting, mapping, and/or characterizing surface features, the article 160 may be sequentially rotated through a number of azimuthal angles, and the photon emitter 110 may respectively sequentially (or continuously) emit photons onto the surface of the article 160 at each successive azimuthal angle, scattering photons from the surface features of the article 160 for sequential detection by the photon detector array (e.g., photon detector array 130). With respect to continuous detecting, mapping, and/or characterizing surface features, the article 160 may be continuously rotated through a number of azimuthal angles, and the photon emitter 110 may continuously emit photons onto the surface of the article 160, scattering photons from the surface features of the article 160 for continuous (or as near continuous as desired or allowed, for example, by technological limitations of the photon detector array) detection by the photon detector array (e.g., photon detector array 130). Whether by sequential or continuous rotation through the number of azimuthal angles, differential surface features maps such as 170A and 170B, or the information sufficient to produce such surface features maps 160A and 160B, may be used (e.g., contrasted) to qualitatively and/or quantitatively characterize surface features and differentiate such surface features. In practice, any of a number of differential surface features maps (e.g., 160A, 160B, 160C . . . 160n, wherein the index n indicates the nth surface features map), or the information sufficient to produce such surface features maps, may be used to effect the foregoing. In addition, one or more composite surface features map may be generated from the differential surface features maps (or the information sufficient to produce such differential surface features maps), providing one or more composite surface features maps from selected azimuthal angles, including all possible azimuthal angles.

While the rotatable stage 150 of FIGS. 7A and 7B is illustrated to rotate through an azimuthal angle of 90°, the rotatable stage 150 may be configured to rotate through a smaller azimuthal angle (e.g., 1°, 2°, 3°, 5°, 10°, 25°, 45°, etc.) or larger azimuthal angle (e.g., 120°, 180°, etc.) as deemed sufficient for detecting, mapping, and/or characterizing surface features of articles. Furthermore, while the rotatable stage 150 is illustrated in FIGS. 7A and 7B to rotate through a single azimuthal angle, the rotatable stage 150 may be configured to rotate through as many azimuthal angles as deemed sufficient for detecting, mapping, and/or characterizing surface features of articles. Moreover, while the rotatable stage 150 is illustrated in FIGS. 7A and 7B to rotate in an anti-clockwise direction, the rotatable stage 150 may be alternatively configured to rotate in a clockwise direction or even further alternatively configured to rotate in either an anti-clockwise or a clockwise direction.

Turning to FIGS. 7C and 7D, FIG. 7C provides a non-limiting schematic illustrating detection of surface features of articles at a number of azimuthal angles using a number of photon emitters 110A-110D. As illustrated, a photon emitter 110A may be azimuthally positioned at a first azimuthal angle to emit photons onto the surface 162 of the article 160 at the first azimuthal angle without rotation of the article 160; however, in addition to supporting the article, the stage 150 may be configured to rotate the article 160 in some embodiments. The photon emitter 110A may emit photons onto the surface 162 of the article 160 from the first azimuthal angle, scattering photons from surface features such as surface feature 164A in the process. A photon detector array such as photon detector array 130 of FIG. 1A may then detect photons scattered from the surface features such as the surface feature 164A for a first surface features map 170A, or for collection of information sufficient to produce the first surface features map 170A. Signals from the photon detector array may subsequently be used for the first surface features map 170A. FIG. 8A provides an image of such a surface features map 170A at a nominal azimuthal angle of 270°, in which the surface feature 164A is labeled "only 1 defect seen."

FIG. 7D further provides a non-limiting schematic illustrating detection of surface features of articles at a number of azimuthal angles using a number of photon emitters 110A-110D. As illustrated, a photon emitter 110B may be azimuthally positioned at a second azimuthal angle to emit photons onto the surface 162 of the article 160 at the second azimuthal angle without rotation of the article 160. The photon emitter 110B may emit photons onto the surface 162 of the article 160 from the second azimuthal angle, scattering photons from surface features in the process, such as scattering photons from the surface feature 164A, as well as scattering photons from a surface feature 164B. The photon detector array may then detect photons scattered from the surface features such as the surface feature 164A and the surface feature 164B, which surface feature 164B may not have been optimally detected or not detected at all at the first azimuthal angle. As such, by virtue of emitting photons onto the surface of the article through the azimuthal angle α, surface features such as surface feature 164B are better detected or additionally detected. As with first surface features map 170A, photon-detector-array signals from the photon detector array may be used for the second surface features map 170B. FIG. 8B provides an image of such a surface features map 170B at a nominal azimuthal angle of 240°, in which the surface features 164A and 164B are labeled "2 defects seen." In view of the combination of surface features maps 170A and 170B providing better information or more information on surface features of articles than any one of surface features maps 170A and 170B, the number of azimuthal angles at which photons are emitted on the surface of the article increases the sensitivity of the apparatus and/or the certainty that as many of the surface features as possible are identified.

The photon emitters 110A-D illustrated in FIGS. 7C and 7D may be configured to sequentially or simultaneously emit photons onto the surface 162 of the article 160 respectively for piecewise or simultaneous detecting, mapping, and/or characterizing surface features. With respect to piecewise detecting, mapping, and/or characterizing surface features, photons be sequentially emitted onto the surface of the article 160 through a number of azimuthal angles, for example, by photon emitter 110A, followed by photon emitter 110B, followed by photon emitter 110C, and so on, scattering photons from the surface features of the article 160 for sequential detection by the photon detector array (e.g., photon detector array 130). With respect to continuous detecting, mapping, and/or characterizing surface features, photons be simultaneously emitted onto the surface of the article 160 through a number of azimuthal angles, for example, by each of photon emitters 110A-D at the same time, scattering photons from the surface features of the article 160 for detection by the photon detector array (e.g., photon detector array 130). Whether by emitting photons sequentially or simultaneously through the number of azimuthal angles, differential surface features maps such as 170A and 170B, or the information sufficient to produce such surface features maps 160A and 160B, may be used (e.g., contrasted) to qualitatively and/or quantitatively characterize surface features and differentiate such surface features. In practice, any of a number of differential surface features maps (e.g., 160A, 160B, 160C . . . 160n, wherein the index n indicates the nth surface features map), or the information sufficient to produce such surface features maps, may be used to effect the foregoing. In addition, one or more composite surface features map may be generated from the differential surface features maps (or the information sufficient to produce such differential surface features maps), providing one or more composite surface features maps from selected azimuthal angles, including all possible azimuthal angles.

While the number of photon emitters 110A-D of FIGS. 7C and 7D are illustrated to be positioned an azimuthal angle of 90° apart from each other, the number of photon emitters, which are not limited in number, may be positioned a smaller azimuthal angle (e.g., 1°, 2°, 3°, 5°, 10°, 25°, 45°, etc.) apart from each other or a larger azimuthal angle (e.g., 120°, 180°, etc.) apart from each other as deemed sufficient for detecting, mapping, and/or characterizing surface features of articles. Furthermore, while FIGS. 7C and 7D illustrate four photon emitters, the apparatus may include any of a number of photon emitters sufficient to effect the number of azimuthal angles for detecting, mapping, and/or characterizing surface features of articles, examples of the number of photon emitters being provided herein, including the photon emitters 110A-D of FIGS. 7C and 7D. Moreover, while the photon emitters 110A-D of FIGS. 7C and 7D are illustrated to emit photons in an anti-clockwise direction, the number of photon emitters may be alternatively configured to emit photons in a clockwise direction or even further alternatively configured to emit photons in either an anti-clockwise or a clockwise direction.

The apparatus may be configured for detecting, mapping, and/or characterizing surface features of articles, wherein the surface features are nanometer-sized (i.e., admits of nm units as measured) or smaller in their smallest dimension (e.g., length, width, height, or depth, depending on the surface feature), which surface features may be smaller than the wavelength of photons emitted from a photon emitter of the apparatus. However, the apparatus is not limited to surface features of articles that are nanometer-sized or smaller, as the apparatus may be configured for detecting, mapping, and/or characterizing surface features of articles, wherein the surface features are micrometer-sized (i.e., admits of μm units as measured) or larger. In some embodiments, for example, the apparatus may be configured for detecting, mapping, and/or characterizing surface features of articles, wherein the surface features are smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as surface features of articles smaller than 9 Å, 8 Å, 7 Å, 6 Å, 5 Å, 4 Å, 3 Å, 2 Å, or 1 Å in their smallest dimension. In view of the foregoing, and in some embodiments, for example, the apparatus may be configured for detecting, mapping, and/or characterizing surface features of articles, wherein the surface features are between 0.1 nm and 1000 nm, such as between 0.1 nm and 500 nm, including between 0.1 nm and 250 nm, and further including between 0.1 nm and 100 nm, and even further including between 0.1 nm and 80 nm. Furthermore, the apparatus may be configured for detecting, mapping, and/or characterizing subsurface features, such as subsurface defects, wherein the subsurface features have a depth more than 1 nm, 2 nm, 3 nm, 4 nm, 5 nm, 6 nm, 7 nm, 8 nm, 9 nm, or 10 nm, or deeper.

The apparatus may be configured for detecting, mapping, and/or characterizing surface features of articles, including surface and/or subsurface defects including particle contamination in which the particles are nanometer-sized (i.e., admits of nm units as measured) or smaller in their smallest dimension (e.g., length, width, or height). In some embodiments, for example, the apparatus may be configured for detecting, mapping, and/or characterizing surface and/or subsurface particles smaller than 125 nm, such as smaller than 100 nm, including smaller than 80 nm, and further including smaller than 10 nm in their smallest dimension. Detecting, mapping, and/or characterizing surface and/or subsurface particles down to the level of 10 nm in height is important for hard disks of hard disk drives, as particles greater than 10 nm in height (e.g., from the surface) may corrupt the spacing between the hard disk and the read-write head of a hard disk drive. In some embodiments, for example, the apparatus may be configured for detecting, mapping, and/or characterizing surface and/or subsurface particles as small as or smaller than 4 nm in height.

The apparatus may be configured for detecting, mapping, and/or characterizing surface features of articles, including surface and/or subsurface defects including scratches (e.g., circumferential scratches) that are micrometer-sized (i.e., admits of μm units as measured) or smaller, such as nanometer-sized (i.e., admits of nm units as measured) or smaller, such as angstrom-sized (i.e., admits of Å units as measured) or smaller, in their smallest dimension (e.g., length, width, or depth). With respect to micrometer-sized scratches, the apparatus may be configured for detecting, mapping, and/or characterizing scratches from, for example, 1 μm to 1000 μm in length, which may be significantly longer than the wavelength of photons emitted from a photon emitter of the apparatus. In some embodiments, for example, the apparatus may be configured for detecting, mapping, and/or characterizing scratches smaller than 1000 μm, such as smaller than 500 μm, including smaller than 250 μm, further including smaller than 100 μm, and even further including smaller than 50 μm in scratch length. With respect to nanometer-sized scratches, the apparatus may be configured for detecting, mapping, and/or characterizing scratches from, for example, 1 nm to 500 nm in scratch width. In some embodiments, for example, the apparatus may be configured for detecting, mapping, and/or characterizing scratches smaller than 500 nm, such as smaller than 250 nm, including smaller than 100 nm, further including smaller than 50 nm, and even further including smaller than 15 nm in scratch width. Surprisingly, due to a high level of spatial coherence, the apparatus may be configured for detecting, mapping, and/or characterizing angstrom-sized scratches with respect to scratch depth. In some embodiments, for example, the apparatus may be configured for detecting, mapping, and/or characterizing scratches smaller than 50 Å, such as smaller than 25 Å, including smaller than 10 Å, further including smaller than 5 Å, and even further including smaller than 1 Å (e.g., 0.5 Å) in scratch depth. For example, the apparatus may be configured for detecting, mapping, and/or characterizing scratches smaller than 500 μm in length, smaller than 100 nm in width, and smaller than 50 Å in depth.

The apparatus may be operable to accurately and/or precisely map or otherwise determine the position of a surface feature (e.g., FIGS. 6A [top] and 6B [top]) on an article's surface. With respect to accuracy, the apparatus may be operable to map or otherwise determine the position of a feature on an article's surface within a micrometer-sized (i.e., admits of μm units as measured) radius or better. In some embodiments, for example, the apparatus may be operable to accurately map or otherwise determine the position of a feature on an article's surface within a radius of 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, 4 μm, 3 μm, 2 μm, or 1 μm, or better. Combinations of the foregoing may also be used to describe the accuracy with which the apparatus may map or otherwise determine the position of a feature on an article's surface. In some embodiments, for example, the apparatus may be operable to accurately map or otherwise determine the position of a feature on an article's surface within a radius ranging from 1 μm to 100 μm, such as from 1 μm to 50 μm, including from 1 μm to 30 μm, and further including from 5 μm to 10 μm.

In addition to accurately and/or precisely mapping or otherwise determining the position of a feature on a surface of an article, the apparatus may be operable to accurately and/or precisely determine the photon scattering intensity distribution (e.g., FIGS. 6A [bottom] and 6B [bottom]) of the feature on the surface of the article. Such a photon scattering intensity distribution may be used characterize a surface feature of an article both quantitatively and qualitatively.

With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, or the number of surface features per unit area per article, as well as the number of each type of surface feature on the article. Such characterization information may be cataloged across a number of articles and be used to correct manufacturing trends should such features include surface and/or subsurface defects that might degrade the performance of the article.

With respect to qualitative characterization of a surface feature of an article, qualitative characterization may include a determination of the morphology, form, or shape of the surface feature of the article, including whether the surface feature is a particle, a stain, a scratch, or a void, etc., which determination may be effected by, but is not limited to, analysis of photon scattering intensity distributions. Qualitative characterization may further include chemical characterization of surface features known to differentially scatter photons such as, but not limited to, certain oxides, which may have faceted surfaces that differentially and/or directionally scatter photons. Qualitative characterization may even further include distinguishing between surface features known to differentially scatter photons with respect to wavelength; a polarization filter may be used to distinguish between surface features known to differentially scatter photons with respect to polarization; a coherence filter may be used to distinguish between surface features known to differentially scatter photons with respect to coherence; and a phase filter or waveplate may be used to distinguish between surface features known to differentially scatter photons with respect to phase. In some embodiments, for example, qualitative characterization of one or more surface features of an article may include contrasting photon-scattering information in the effective absence of one of the foregoing filters with photon-scattering information using one or more of the foregoing filters or contrasting a first surface features map produced in the effective absence of one of the foregoing filters with a second surface features map (or a number of surface features maps) produced using one or more of the foregoing filters. Along with quantitative characterization information, such qualitative characterization information may be cataloged across a number of articles and be used to correct manufacturing trends should such features include surface and/or subsurface defects that might degrade the performance of the article.

The apparatus described herein may be configured to process or inspect articles at a rate greater than or commensurate with the rate at which the articles or workpieces thereof are produced. In some embodiments, for example, the apparatus may be configured to process or inspect articles at a rate of at least 1, 2, 3, 4, 5, 6, 7, 8, 9, 10, 12, 14, 16, 18, or 20, or higher, article(s) per second, which rate may be commensurate with the rate at which the articles or workpieces thereof are produced. In some embodiments, for example, the apparatus may be configured to process or inspect articles at a rate of no more than 20, 18, 16, 14, 12, 10, 9, 8, 7, 6, 5, 4, 3, 2, or 1 article(s) per second, which rate may be commensurate with the rate at which the articles or workpieces thereof are produced. Combinations of the foregoing may also be used to describe the rate at which the articles or workpieces thereof are processed or inspected by the apparatus. In some embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, with a number of photon emitters such as photon emitters 110A-D of FIGS. 7C and 7D, an article such as a hard disk of a hard disk drive need not be rotated during processing or inspecting. As such, the apparatus may be configured to hold an article stationary while emitting photons onto the surface of the article.

As such, provided herein is an apparatus, comprising a photon emitting means configured to emit photons onto a surface of an article at a plurality of azimuthal angles; a photon detector array configured to receive photons scattered from surface features of the article; and a processing means configured to 1) process photon-detector-array signals corresponding to the photons scattered from the surface features of the article and 2) morphologically characterize the surface features of the article. In some embodiments, the apparatus further comprises a telecentric lens coupled to the photon detector array. In some embodiments, the processing means is further configured to generate at least one surface features map for the article from the photon-detector-array signals corresponding to the photons scattered from the surface features of the article. In some embodiments, the processing means is further configured to generate a plurality of surface features maps for the article from the photon-detector-array signals corresponding to the photons scattered from the surface features of the article, wherein the plurality of surface features maps respectively correspond to the plurality of azimuthal angles. In some embodiments, the processing means comprises one or more computers or equivalent devices configured to process the photon-detector-array signals corresponding to the photons scattered from the surface features of the article. In some embodiments, the photon emitting means comprises at least one photon emitter and a stage configured to support the article. In some embodiments, the stage is further configured for rotating and azimuthally positioning the article with respect to the at least one photon emitter, wherein azimuthally positioning the article with respect to the at least one photon emitter allows for emitting photons onto the surface of the article at the plurality of azimuthal angles. In some embodiments, a plurality of photon emitters are respectively positioned around the stage at the plurality of azimuthal angles for emitting photons onto the surface of the article at the plurality of azimuthal angles.

Also provided herein is an apparatus, comprising a photon emitting means configured to emit photons onto a surface of an article at a plurality of azimuthal angles; and a processing means configured to 1) process photon-detector-array signals corresponding to photons scattered from surface features of the article and 2) generate one or more surface features maps for the article from the photon-detector-array signals corresponding to the photons scattered from the surface features of the article. In some embodiments, the apparatus further comprises a telecentric lens coupled to a photon detector array. In some embodiments, the one or more surface features maps comprises a plurality of surface features maps respectively corresponding to the plurality of azimuthal angles. In some embodiments, the one or more surface features maps comprises a composite surface features map of a plurality of surface features maps respectively corresponding to the plurality of azimuthal angles. In some embodiments, the processing means comprises one or more computers or equivalent devices configured to process the photon-detector-array signals corresponding to the photons scattered from the surface features of the article. In some embodiments, the photon emitting means comprises at least one photon emitter and a rotatable stage configured for supporting and azimuthally positioning the article with respect to the at least one photon emitter, wherein azimuthally positioning the article with respect to the at least one photon emitter allows for emitting the photons onto the surface of the article at the plurality of azimuthal angles.

Also provided herein is an apparatus, comprising a photon detector array comprising a plurality of photon detectors configured to receive photons scattered from surface features of an article; and a processor configured to 1) process photon-detector-array signals corresponding to the photons scattered from the surface features of the article and 2) generate a plurality of surface features maps for the article from the photon-detector-array signals corresponding to the photons scattered from the surface features of the article, wherein the plurality of surface features maps respectively correspond to a plurality of azimuthal angles at which photons are emitted onto a surface of the article. In some embodiments, the apparatus further comprises a telecentric lens coupled to the photon detector array. In some embodiments, the processor is further configured to generate a composite surface features map for the article from the plurality of surface features maps for the article. In some embodiments, the processor is of one or more computers or equivalent devices configured to process the photon-detector-array signals corresponding to the photons scattered from the surface features of the article. In some embodiments, the apparatus further comprises a photon emitting means for emitting photons onto the surface of the article at the plurality of azimuthal angles. In some embodiments, the photon emitting means comprises at least one photon emitter and a rotatable stage configured for supporting and azimuthally positioning the article with respect to the at least one photon emitter, wherein azimuthally positioning the article with respect to the at least one photon emitter allows for emitting the photons onto the surface of the article at the plurality of azimuthal angles.

While some particular embodiments have been described and/or illustrated herein, and while these particular embodiments have been described and/or illustrated in considerable detail, it is not the intention of the applicant(s) for these particular embodiments to limit the scope of the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts provided herein. The implementations provided herein and other implementations are within the scope of the following claims

What is claimed is:

1. An apparatus comprising:
a photon emitter configured to emit photons onto a surface of an article at an azimuthal angle and with an emitting wavelength, wherein the photon emitter is positioned at an emitting distance from the surface of the article;
a photon detector array configured to receive photons scattered from surface features of the article at a reflective azimuthal angle with a reflecting wavelength, wherein the photon detector array is positioned at a receiving distance from the surface of the article; and
a processing unit configured to process a plurality of photon-detector-array signals corresponding to the photons scattered from the surface features of the article and morphologically characterize the surface features of the article based on the azimuthal angle, the emitting wavelength, the reflective azimuthal angle, the reflecting wavelength, the emitting distance, and the receiving distance to distinguish between different surface feature types.

2. The apparatus of claim 1, wherein the different surface features types includes a particle, stain, scratch, and void surface features.

3. The apparatus of claim 1, wherein the morphologically characterizing the surface features is further based on polarization, coherency, and phase associated with the emitting photons and the received photons.

4. The apparatus of claim 1, wherein the photon emitter comprises a light emitting diode (LED) based ring configured to enhance circumferential scratches and voids on the surface of the article by emitting photons at a glancing angle of less than 45°.

5. The apparatus of claim 1, wherein the photon emitter is further configured to emit photons onto the surface of the article at a different azimuthal angle subsequent to emitting photons at the azimuthal angle through gradational rotation of the article, and wherein the photon detector array is further configured to receive photons scattered from the surface features of the article at a different reflective azimuthal angle.

6. The apparatus of claim 1, wherein the processing unit is configured to determine a size associated with each surface feature of the surface features by processing photon scattering intensity distribution associated with the received photons scattered from the surface features of the article.

7. The apparatus of claim 1, wherein the processing unit is further configured to distinguish between the different surface feature types through differential analysis of wavelength and polarization for received photons scattered from the surface features of the article.

8. The apparatus of claim 1, wherein the processing unit is further configured to distinguish between the surface feature types through differential analysis of phase and coherency of photons scattered from the surface features of the article.

9. The apparatus of claim 1 further comprising:
a first component selected from a group consisting of a wavelength filter, a bandpass filter, a polarization filter, a coherence filter, a periodic array tuned filter, and a phase filter, wherein the component is coupled to the photon emitter to alter characteristics of the photons emitted; and
a second component selected from a group consisting of a wavelength filter, a bandpass filter, a polarization filter, a coherence filter, a periodic array tuned filter, and a phase filter, wherein the component is coupled to the photon detector array to alter characteristics of the received photons scattered from the surface features of the article.

10. An apparatus comprising:
a first photon emitter configured to emit photons onto a surface of an article at a first azimuthal angle, with a first emitting wavelength, a first polarization, a first coherency, and a first phase, wherein the first photon emitter is positioned at a first distance from the surface of the article;
a second photon emitter configured to emit photons onto a surface of an article at a second azimuthal angle, with a second emitting wavelength, a second polarization, a second coherency, and a second phase, wherein the second photon emitter is positioned at a second distance from the surface of the article,
and wherein the first distance, the first azimuthal angle, the first emitting wavelength, the first polarization, the first coherency and the first phase are different from the second distance, the second azimuthal angle, the second emitting wavelength, the second polarization, the second coherency and the second phase respectively to distinguish between feature types on the surface of the article;
a photon detector array configured to receive photons scattered from surface features of the article at a plurality of reflective azimuthal angles, a plurality of reflective wavelengths, a plurality of reflective polarizations, a plurality of reflective coherencies, and a plurality of reflective phases, wherein the photon detector array is positioned at a receiving distance from the surface of the article; and
a processing unit configured to process a plurality of photon-detector-array signals corresponding to the photons scattered from the surface features of the article and morphologically characterize the surface features of the article based on the distance, azimuthal angle, wavelength, polarization, coherency, and phase associated with photons of the first photon emitter, the second photon emitter, and the photon detector array to distinguish between different surface feature types.

11. The apparatus of claim 10, wherein the different surface features types includes a particle, stain, scratch, and void surface features.

12. The apparatus of claim 10, wherein the first photon emitter comprises a light emitting diode (LED) based ring configured to enhance circumferential scratches and voids on the surface of the article by emitting photons at a glancing angle of less than 45°.

13. The apparatus of claim 10, wherein the processing unit is configured to determine a size associated with each surface feature of the surface features by processing photon scattering intensity distribution associated with the received photons scattered from the surface features of the article.

14. The apparatus of claim 10, wherein the processing unit is further configured to distinguish between the different surface feature types through differential analysis of wavelength and polarization for received photons scattered from the surface features of the article.

15. The apparatus of claim 10, wherein the processing unit is further configured to distinguish between the surface feature types through differential analysis of phase and coherency of photons scattered from the surface features of the article.

16. The apparatus of claim 10 further comprising:
a first component coupled to the first photon emitter, wherein the first component comprises a wavelength filter, a polarization filter, a coherence filter, and a phase filter to emit photons at the first wavelength, the first polarization, the first coherency, and the first phase;
a second component coupled to the second photon emitter, wherein the second component comprises a wavelength filter, a polarization filter, a coherence filter, and a phase filter to emit photons at the second wavelength, the second polarization, the second coherency, and the second phase; and
a third component coupled to the photon detector array, wherein the third component comprises a plurality of wavelength filters, a plurality of polarization filters, a plurality of coherence filters, and a plurality of phase filters to detect scattered photons at the plurality of reflective wavelengths, the plurality of reflective polarizations, the plurality of reflective coherencies, and the plurality of reflective phases.

17. An apparatus comprising:
a photon emitter, at a first instance in time, configured to emit photons onto a surface of an article at a first azimuthal angle, with a first emitting wavelength, a first polarization, a first coherency, and a first phase, wherein the first photon emitter is positioned at a first distance from the surface of the article at the first instance in time, and wherein the photon emitter at a second instance in time subsequent to the first instance in time is configured to emit photons onto the surface of the article at a second azimuthal angle, with a second emitting wavelength, a second polarization, a second coherency, and a second phase, wherein the photon emitter is positioned at a second distance from the surface of the article at a second instance in time;
a photon detector array configured to receive photons scattered from surface features of the article at a plurality of reflective azimuthal angles, a plurality of reflective wavelengths, a plurality of reflective polarizations, a plurality of reflective coherencies, and a plurality of reflective phases, wherein the photon detector array is positioned at a receiving distance from the surface of the article; and
a processing unit configured to process a plurality of photon-detector-array signals corresponding to the photons scattered from the surface features of the article and morphologically characterize the surface features of the article based on the distances, azimuthal angles, wavelengths, polarizations, coherencies, and phases associated with photons of the photon emitter, and the photon detector array to distinguish between different surface feature types.

18. The apparatus of claim 17, wherein the photon emitter comprises a light emitting diode (LED) based ring configured to enhance circumferential scratches and voids on the surface of the article by emitting photons at a glancing angle of less than 45°.

19. The apparatus of claim 17, wherein the processing unit is configured to determine a size associated with each surface feature of the surface features by processing photon scattering intensity distribution associated with the received photons scattered from the surface features of the article.

20. The apparatus of claim 17, wherein the processing unit is further configured to identify chemical characterization of oxides of the surface features.

\* \* \* \* \*